United States Patent [19]

Shimizu et al.

[11] Patent Number: 4,966,900
[45] Date of Patent: Oct. 30, 1990

[54] CEPHALOSPORIN β-LACTAM COMPOUND AND MEDICINAL COMPOSITION

[75] Inventors: Shigeo Shimizu; Hiroyuki Takano, both of Mukawa, Japan

[73] Assignees: Sankei Pharmaceutical Company Ltd., Tokyo; Nippon Pharmaceutical Development Institute Co., Ltd., Hokkaido, both of Japan

[21] Appl. No.: 75,412

[22] Filed: Jul. 20, 1987

[30] Foreign Application Priority Data

Jul. 21, 1986 [JP] Japan .................. 61-169860
Nov. 17, 1986 [JP] Japan .................. 61-273182

[51] Int. Cl.$^5$ .................. C07D 501/36; A61K 31/545
[52] U.S. Cl. ........................ 514/206; 540/222; 540/225; 540/227; 540/226; 514/207
[58] Field of Search ................ 540/222, 227, 228; 514/202, 205, 206

[56] References Cited

U.S. PATENT DOCUMENTS

| | | | |
|---|---|---|---|
| 4,091,671 | 5/1978 | Bruer et al. | 540/222 X |
| 4,278,671 | 7/1981 | Ochiai et al. | 540/227 X |
| 4,694,001 | 9/1987 | Hirata et al. | 540/222 |
| 4,808,711 | 2/1989 | Shimizu et al. | 540/227 |
| 4,826,834 | 5/1989 | Yoshimura et al. | 540/227 |
| 4,866,055 | 9/1989 | Kate et al. | 540/226 |

FOREIGN PATENT DOCUMENTS 0150507 8/1989 European Pat. Off. .

OTHER PUBLICATIONS

Burton et al. Chem. Abstracts vol. 87 (1977), entry 201558h.
Ohnishi, et al. Chem. Abstracts vol. 104 (1986), entry 68678y.

*Primary Examiner*—Nicholas S. Rizzo

*Attorney, Agent, or Firm*—Antonelli, Terry, Stout & Kraus

[57] ABSTRACT

There are disclosed a β-lactam compound represented by the formula (I):

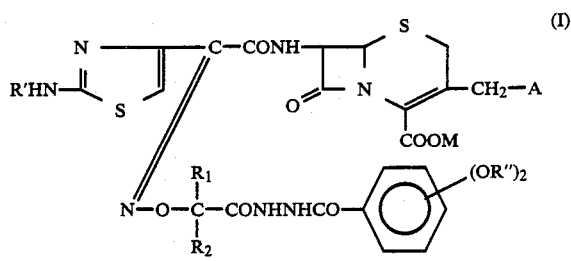

wherein $R_1$ and $R_2$ are independently a hydrogen atom or a lower alkyl group; M is a hydrogen atom, a protective group or an eliminatable group which is easily hydrolyzable in a human body; R' and R" are independently a hydrogen atom or a protective group; A is a mercapto group substituted by a substituted or unsubstituted polycyclic nitrogen-containing heterocyclic ring or a group represented by the following formula (a):

—OOCNR$_3$R$_4$         (a)

where $R_3$ and $R_4$ are independently a hydrogen atom or a lower alkyl group, provided that $R_1$ and $R_2$ are both hydrogen atoms, both $R_3$ and $R_4$ being hydrogen atoms are excluded, or its pharmaceutically acceptable salt, and a method for preparing the same, medicinal composition for microbism therapy containing the same and intermediates for synthesis of the same.

27 Claims, No Drawings

CEPHALOSPORIN β-LACTAM COMPOUND AND MEDICINAL COMPOSITION

BACKGROUND OF THE INVENTION

This invention relates to a novel β-lactam compound, more particularly to a novel cephalosporin series compound useful for antibiotics, a method for preparing the same, a synthetic intermediate and use thereof.

Heretofore, it has been known that a β-lactam series antibiotics has antibacterial activities to gram positive bacteria and gram negative bacteria and many of these compounds have actually been applied therefor. Among them, compounds which are called to as the third aged cephalosporin series antibiotics have wide range of antibacterial spectrum and particularly are evaluated in the clinical field.

However, while the several kinds of the above compounds have been used in practical use, all of them are inferior in their antibiotical activities to *Pseudomonas aeruginosa*. Further, some kinds of them are finely effective to gram negative bacteria other than *Pseudomonas aeruginosa* but there are disadvantages that they have lower activities to gram positive bacteria and also, accompanied with the increased frequency in use of a cephalosporin, cephalosporin acquired strains which are gradually increasing exhibit cross resistance. Further, many kinds of β-lactam series antibiotics are relatively short in half-time in human blood and therefore should be administered twice or three times a day to cause pain to patients in the case of parenteral administration. Accordingly, a development of a βlactam which is long in prolonged time in blood and can be expected to exhibit the effect similar or superior to that of the medicines of the prior art by smaller numbers of administration has been demanded.

SUMMARY OF THE INVENTION

The present inventors have intensively studied, by referring to the above situation, concerning a compound which has potent antibacterial activities in extremely wide ranges, and as a result, have found that the compound represented by the formula (I) has excellent characteristics as a medicinal composition for bacterially infectious disease (microbism) therapy and accomplished the present invention.

That is, the present invention relates to a β-lactam compound represented by the formula (I):

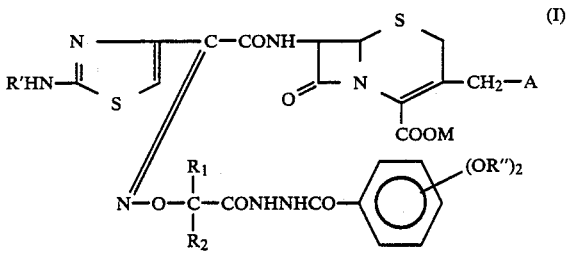

[wherein $R_1$ and $R_2$ are independently a hydrogen atom or a lower alkyl group; M is a hydrogen atom, a protective group or an eliminatable group which is easily hydrolyzable in a human body; R' and R" are independently represent a hydrogen atom or a protective group; A is a mercapto group which is substituted by a substituted or unsubstituted polycyclic nitrogen-containing heterocyclic ring or a group represented by the following formula (a):

$$-OOCNR_3R_4 \quad (a)$$

(wherein $R_3$ and $R_4$ are independently a hydrogen atom or an lower alkyl group, provided that when $R_1$ and $R_2$ are both hydrogen atoms, both $R_3$ and $R_4$ being hydrogen atoms are excluded), or its pharmaceutically acceptable salt, a method for preparing the same, a synthetic intermediate thereof and a medicinal composition for microbism therapy containing said compound as its active ingredient.

Further, hydrates or organic solvates of the compound represented by the above formula (I) are included in the scope of the present invention as a matter of course.

DESCRIPTION OF THE PREFERRED EMBODIMENTS

Next, each groups which are summarily shown in the above formula (I) are explained in more detail.

Explanation of $R_1$, $R_2$ and R'

$R_1$ and $R_2$ are independently a hydrogen atom or a lower alkyl group. R' is a hydrogen atom or a protective group.

In the above, the lower alkyl group includes straight or branched alkyl groups having 1 to 3 carbon atoms such as a methyl group, an ethyl group, an n- or iso-propyl group, etc. The protective group represented by R' includes a diphenylmethyl group, a t-butyl group, a p-nitrobenzyl group, a trimethylsilyl group, etc.

Explanation of R"

As the protective group, there may be mentioned, for example, a lower acyl group such as an acetyl group, a propionyl group, etc.; and a lower alkoxycarbonyl group such as a methoxycarbonyl group, an ethoxycarbonyl group, etc.

Explanation of M

M is a hydrogen atom, a protective group or an eliminable group which is easily hydrolyzable in a human body.

When the M is a protective group, there may be mentioned a diphenylmethyl group, a t-butyl group, a p-nitrobenzyl group, a trimethylsilyl group, etc.

Further, when the M is an eliminable group which is easily hydrolyzable in a human body, there may be mentioned an acetoxymethyl group, an α-acetoxyethyl group, a pivaroyloxymethyl group, an α-ethoxycarbonyloxymethyl group, an α-methoxycarbonyloxymethyl group, an α-methoxycarbonyloxyethyl group, an α-ethoxycarbonyloxyethyl group, a 1-indanyl group, a phthalidyl group, a 5-methyl-2-oxo 1,3-dioxol-4-ylmethyl group and the like.

Explanation of A

When the A is represented by the formula: (a) $-OOCNR_3R_4$, the lower alkyl group represented by $R_3$ and $R_4$ is as defined above for $R_1$ and $R_2$.

Further, the A may be a mercapto group substituted by a substituted or unsubstituted polycyclic nitrogen-containing heterocyclic ring. Such a mercapto group substituted by a heterocyclic ring may be mentioned, for example, the following formula (b), (c), or (d) or (e):

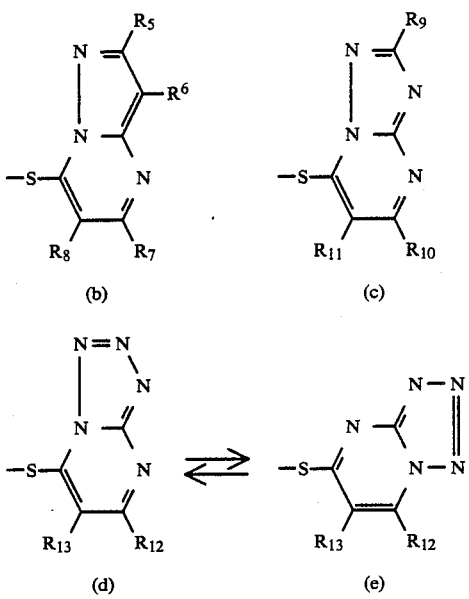

In case where the A is represented by the above formula (b), (c), or (d) or (e), $R_5$, $R_6$, $R_7$, $R_8$, $R_9$, $R_{10}$, $R_{11}$, $R_{12}$ and $R_{13}$ represent independently a hydrogen atom, a lower alkyl group which may be substituted by a halogen atom, a cycloalkyl group or a carboxyl group which may be substituted by a protective group or an eliminatable group which is easily hydrolyzable in a human body and further, $R_7$ and $R_8$, $R_{10}$ and $R_{11}$, and $R_{12}$ and $R_{13}$ may be combined with each other, respectively, to form an alkylene group having 3 to 4 carbon atoms, provided that $R_1$ and $R_2$ are both hydrogen atoms, both $R_3$ and $R_4$ being hydrogen atoms are excluded. Further, the above formulae (d) and (e) have tautomerismic relation to each other.

In the above, as the lower alkyl group which may be substituted by a halogen atom, there may be mentioned, for example, a methyl group, an ethyl group, an n- or iso-propyl group, a monofluoromethyl group, a difluoromethyl group, a trifluoromethyl group, a monofluoroethyl group, a difluoroethyl group, a trifluoroethyl group, etc. The cycloalkyl group may include, for example, a cyclopropyl group, a cyclobutyl group, a cyclopentyl group, a cyclohexyl group, etc. The protective group and the eliminatable group in the carboxyl group which may be substituted by the protective group or the eliminable group which is easily hydrolyzable in a human body have the same meanings as the groups defined above as the M. The alkylene group having 3 to 4 carbon atoms may include, for example, a propylene group, a butylene group etc.

Furthermore, when the A is the group represented by the above formula (b), (c) or (d) or (e), specific examples thereof may include the following groups:
(Pyrazolo[1,5-a]pyrimidine-7-yl)thio,
(3-Carboxypyrazolo[1,5-a]pyrimidine-7-yl)thio,
(3-Carboxy-5-methylpyrazolo[1,5-a]pyrimidine-7-yl)thio,
(3-Carboxy-5,6-dimethylpyrazolo[1,5-a]pyrimidine-7-yl)thio,
(3-Carboxy-6,7-dihydro-5H-cyclopenta[f]pyrazolo[1,5-a]-pyrimidine-8-yl)thio,
(5-Methylpyrazolo[1.5-a]pyrimidine-7-yl)thio,
(s-Triazolo[1,5-a]pyrimidine-7-yl)thio,
(5-Methyl-s-triazolo[1,5-a]pyrimidine-7-yl)thio,
(2-Carboxy-s-triazolo[1,5-a]pyrimidine-7-yl)thio,
(2-Cyclopentyl-s-triazolo[1,5-a]pyrimidine-7-yl)thio,
(2-Carboxy-5-methyl-s-triazolo[1,5-a]pyrimidine-7-yl)thio,
(5-Carboxy-2-methyl-s-triazolo[1,5-a]pyrimidine-7-yl)thio,
(5,6-Dimethyl-s-triazolo[1,5-a]pyrimidine-7-yl)thio,
(5-Carboxy-2-ethyl-s-triazolo[1,5-a]pyrimidine-7-yl)thio,
(5-Carboxy-2-cyclopentyl-s-triazolo[1,5-a]pyrimidine-7-yl)thio,
(5-Carboxy-2-trifluoromethyl-s-triazolo[1,5-a]pyrimidine-7-yl)thio,
(2-Carboxy-5,6-dimethyl-s-triazolo[1,5-a]pyrimidine-7-yl)thio,
(5,6-Dimethyl-2-trifluoromethyl-s-triazolo[1,5-a]pyrimidine-7-yl)thio,
(6,7-Dihydro-5H-cyclopenta[f]-s-triazolo[1,5-a]pyrimidine-8-yl)thio,
(2-Carboxy-6,7-dihydro-5H-cyclopenta[f]-s-triazolo[1,5-a]-pyrimidine-8-yl)thio,
(6,7-Dihydro-2-methyl-5H-cyclopenta[f]-s-triazolo[1,5-a]-pyrimidine-8-yl)thio,
(6,7-Dihydro-2-trifluoromethyl-5H-cyclopenta[f]-s-triazolo[1,5-a]pyrimidine-8-yl)thio,
(5,6,7,8-Tetrahydro-s-triazolo[5,1-b]quinazoline-9-yl)thio,
(5,6,7,8-Tetrahydro-2-methyl-s-triazolo[5,1-b]quinazoline-9-yl)thio,
(5,6,7,8-Tetrahydro-2-trifluoromethyl-s-triazolo[5,1b-]quinazoline-9-yl)thio,
(2-Carboxy-5,6,7,8-tetrahydro-s-triazolo[5,1-b]quinazoline-9-yl)thio,
(5-Methyl-2-trifluoromethyl-s-triazolo[1,5-a]pyrimidine-7-yl)thio,
(2-Cyano-5-methyl-s-triazolo[1,5-a]pyrimidine-7-yl)thio,
(2-Carboxy-5-trifluoromethyl-s-triazolo[1,5-a]pyrimidine-7-yl)thio,
(5-Methyltetrazolo[1,5-a]pyrimidine-7-yl)thio,
(5,6-Dimethyltetrazolo[1,5-a]pyrimidine-7-yl)thio,
(5-Methyl-6-ethyltetrazolo[1,5-a]pyrimidine-7-yl)thio,
(5-Carboxytetrazolo[1,5-a]pyrimidine-7-yl)thio,
(5-Carboxy-2-methylpyrazolo[1,5-a]pyrimidine-7-yl)thio,
(3-Carboxy-5-trifluoromethylpyrazolo[1,5-a]pyrimidine-7-yl)thio,
(3,5-Dicarboxypyrazolo[1,5-a]pyrimidine-7-yl)thio,
(2,5-Dimethylpyrazolo[1,5-a]pyrimidine-7-yl)thio,
(3,5-Dimethylpyrazolo[1,5-a]pyrimidine-7-yl)thio,
(3-Carboxy-5,6,7,8-tetrahydropyrazolo[5,1-b]quinazoline-9-yl)thio,
(6-Carboxy-s-triazolo[1,5-a]pyrimidine-7-yl)thio,
(6 Carboxy-2-methyl-s-triazolo[1,5-a]pyrimidine-7-yl)thio,
(6-Carboxy-2 trifluoromethyl-s-triazolo[1,5-a]pyrimidine-7-yl)thio,
(6-Carboxy-2-cyclopentyl-s-triazolo[1,5-a]pyrimidine-7-yl)thio,
(5-Monofluoromethyl-s-triazolo[1,5-a]pyrimidine-7-yl)thio,
(2-Carboxy-5-monofluoromethyl-s-triazolo[1,5-a]pyrimidine-7-yl)thio, and
(5-Carboxy-2-monofluoromethyl-s-triazolo[1,5-a]pyrimidine-7-yl)thio.

As the pharmaceutically acceptable salts of the β-lactam compounds according to the present invention, there may be mentioned alkali metal salts such as of sodium salts, potassium salts, etc.; alkaline earth metal salts such as of magnesium salts, calcium salts, etc.; ammonium salts; salts with organic bases such as of diisopropylamine, benzylamine, triethanolamine, triethylamine, N-methylmorpholine, pyridine, piperazine, etc.; salts with organic acids such as of acetic acid, formic acid, maleic acid, fumaric acid, methanesulfonic acid, p-toluenesulfonic acid, etc.; salts with inorganic acids such as of hydrochloric acid, hydrobromic acid, sulfuric acid, phosphoric acid and the like.

Manufacturing methods of the novel β-lactam compounds

The novel β-lactam compounds to be intended in the present invention can be synthesized according to the following three methods.

The first method

The title compound can be obtained by reacting the compound represented by the formula (II):

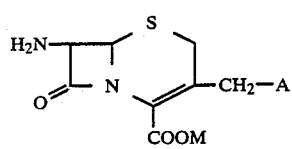

wherein symbols in the formula are the same as mentioned above, with the carboxylic acid represented by the formula (III):

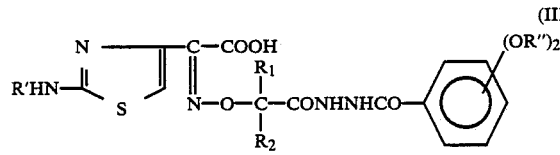

wherein symbols in the formula are the same as mentioned above, or its reactive derivative and removing a protective group, if necessary.

In this method, the compound represented by the formula (III) which is used as a starting compound can be synthesized as shown below.

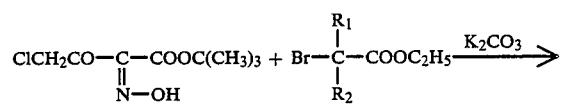

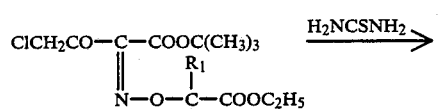

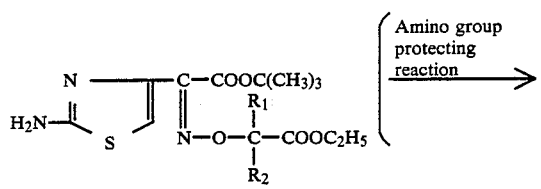

-continued

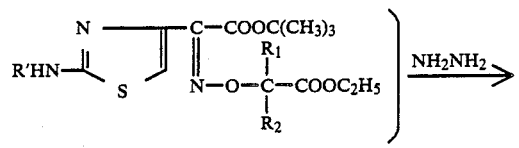

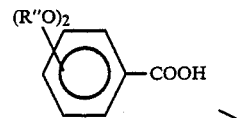

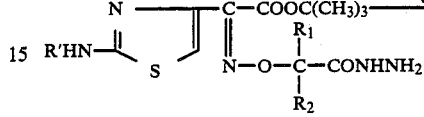

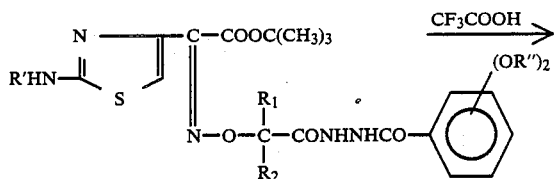

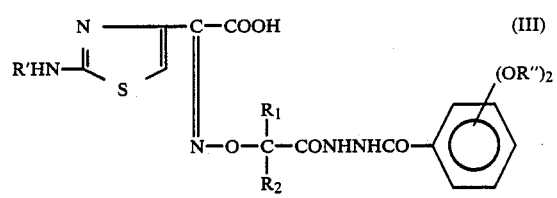

wherein symbols in the formula are the same as mentioned above.

The second method

The title compound can be obtained by reacting the compound represented by the formula (IV):

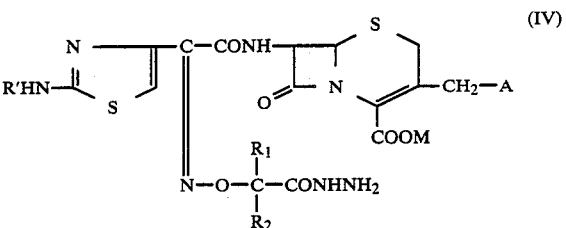

wherein symbols in the formula are the same as mentioned above, with the compound represented by the formula (V):

or its reactive derivative and removing a protective group, if necessary.

In this method, the starting compound represented by the formula (IV) is a novel compound, and an example of the synthesizing method is shown by referring reaction schemes in the following:

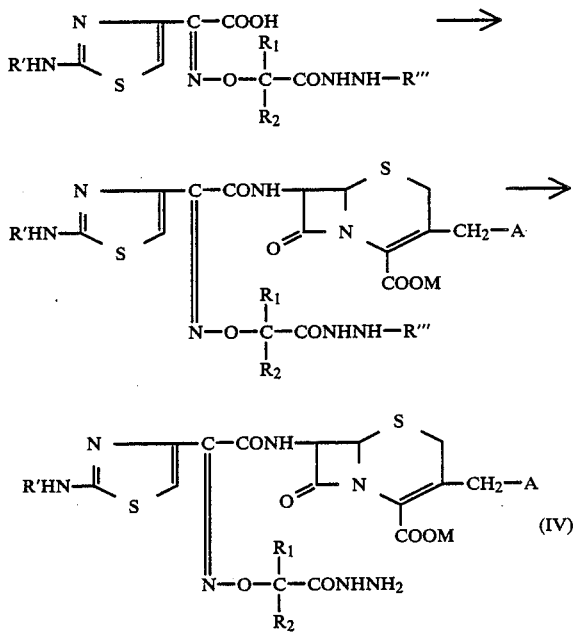

wherein R" is a protective group and the other symbols are the same as mentioned above.

The third method

The compound represented by the formula (I'):

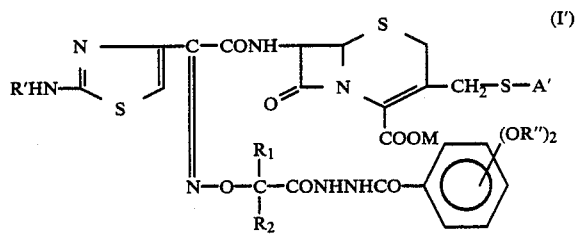

wherein A' is a substituted or unsubstituted polycyclic nitrogen-containing heterocyclic ring; $R_1$, $R_2$, M and R' are the same as mentioned above, can be obtained by reacting the compound represented by the formula (VI):

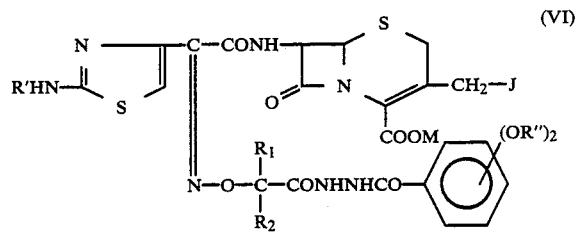

wherein J represents a halogen atom or an acetoxy group and the other symbols are the same as mentioned above, with the compound represented by the formula (VII):

A'—SH     (VII)

wherein A' has the same meanings as defined above, and by removing a protective group, if necessary. Further, the compounds represented by the formulae (VII) and (VIII) have tautomerismic relation to each other.

In the following, producing methods of the novel β-lactam compounds according to the present invention will be explained in more detail.

The first method

Specific examples of the compound represented by the formula (III) may include, for example, the following compounds:

2-(2-Amino-1,3-thiazol-4-yl)-2-{1-[3-(3,4-dihydroxybenzoyl)carbazoyl]-1-methylethoxyimino}acetic acid, 2-(2-Amino-1 3-thiazol-4-yl)-2-{1-[3-(3,4-dihydroxybenzoyl)carbazoyl]ethoxyimino}acetic acid, 2-(2-Amino-1,3-thiazol-4-yl)-2-{[3-(3,4-dihydroxybenzoyl)carbazoyl]methoxyimino}acetic acid, 2-(2-Amino-1,3-thiazol-4-yl)-2-{1-[3-(3,4-diacetoxybenzoyl)carbazoyl]-1-methylethoxyimino}acetic acid, 2-(2-Amino-1,3-thiazol-4-yl)-2-{1-[3-(3,4-diacetoxybenzoyl)carbazoyl]ethoxyimino}acetic acid, 2-(2-Amino-1,3-thiazol-4-yl)-2-{[3-(3,4-diacetoxybenzoyl)carbazoyl]methoxyimino}acetic acid.

The reaction between the compound (II) and the compound (III) should desirably be carried out, in general, by using reactive derivatives of the compound (III) as the compound (III). In this case, it is desirable to protect previously the hydroxyl group as an acyl ester. As the reactive derivatives, there may be mentioned, for example, acid halides, mixed acid anhydrides, active esters and the like. Further, while free carboxylic acids can be used as such, suitable condensation reagent may desirably be used in this case. As the reagent, there may be employed, for example, N,N'-dicyclohexylcarbodiimide (DCC), N,N'-carbonyldiimidazole, cyanuric chloride, Vilsmeier reagent and the like. Such reactions have been known in the field of penicillin chemistry, cephalosporin chemistry and peptide chemistry. The equimolar amounts of the compounds (II) and (III) are employed in general.

These reactions are usually carried out at −10° to 30° C. for about 0.5 to 2 hours in a suitable solvent such as methylene chloride, chloroform, tetrahydrofuran, dioxane, dimethylformamide, dimethylacetamide, acetonitrile, acetone, water or mixed solvents of the above. Treatments after the reaction can be carried out by the methods well known in the art such as separation, purification and the like.

The second method

Specific examples of the compound represented by the formula (IV) may include, for example, the following compounds:

7-{2-[2-Amino-1,3-thiazol-4-yl]-2-(1-hydrazinocarbonyl-1-methylethoxyimino)acetamido}-3-carbamoyloxymethyl-3-cephem-4-carboxylic acid, 7-{2-[2-Amino-1,3-thiazol-4-yl]-2-(1-hydrazinocarbonyl-1-methylethoxyimino)acetamido}-3-[(2-carboxy-5-methyl-s-triazolo[1,5-a]pyrimidin-7-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(3-carboxy-5-methylpyrazolo[1,5-a]pyrimidin-7-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(5-methyltetrazolo[1,5-a]pyrimidin-7-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(2-carboxy- 6,7-dihydro-5H-cyclopenta[f]-s-triazolo[1,5-a]pyrimidin-8-yl)thiomethyl]-3-cephem-4-carboxylic acid,
7-{2-[2-Amino-1,3-thiazol-4-yl]-2-(1-hydrazinocarbonyl-1-methylethoxyimino)acetamido}-3-[(6,7-dihydro-5H-cyclopenta[f]-s-triazolo[1,5-a]pyrimidin-8-yl)thiomethyl]-3-cephem-4-carboxylic acid,
7-{2-[2-Amino-1,3-thiazol-4-yl]-2-(1-hydrazinocarbonyl-1-methylethoxyimino)acetamido}-3-[(5-carboxy-2-methyl-s-triazolo[1,5-a]pyrimidin-7-yl)thiomethyl]-3-cephem-4-carboxylic acid,
7-{2-[2-Amino-1,3-thiazol-4-yl]-2-(1-hydrazinocarbonyl-1-methylethoxyimino)acetamido}-3-[(3-carboxy-5,6-dimethylpyrazolo[1,5a]pyrimidin-7-yl)thiomethyl]-3-cephem-4-carboxylic acid,
7-{2-[2-Amino-1,3-thiazol-4-yl]-2-(1-hydrazinocarbonyl-1-methylethoxyimino)acetamido}-3-[(3-carboxy-6,7-dihydro-5H-cyclopenta[f]pyrazolo[1,5-a]pyrimidin-8-yl)thiomethyl]-3-cephem-4-carboxylic acid,
7-{2-[2-Amino-1,3-thiazol-4-yl]-2-(1-hydrazinocarboxyl-1-methylethoxyimino)acetamido}-3-[(3-carboxypyrazolo[1,5-a]pyrimidin-7-yl)thiomethyl]-3-cephem-4-carboxylic acid,
7-{2-[2-Amino-1,3-thiazol-4-yl]-2-(hydrazinocarbonyl-1-methylethoxyimino)acetamido}-3-[(2-carboxy[1,2,4]triazolo[1,5-a]pyrimidin-7-yl)thiomethyl]-3-cephem-4-carboxylic acid.

The reaction of the compound (IV) and

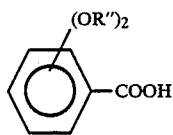

is carried out by allowing the latter as such or the hydroxyl group protected as an acyl ester to react as acid halides, mixed acid anhydrides or active esters, or suitable condensation reagents such as N,N'-dicyclohexylcarbodiimide (DCC), N,N'-carbonyldiimidazole, cyanuric chloride, Vilsmeier reagent and the like can be employed. These reactions can be carried out in a suitable solvent such as methylene chloride, chloroform, tetrahydrofuran, dioxane, dimethylformamide, dimethylacetamide, acetonitrile, acetone, water or mixed solvents of the above, at about $-10°$ to $50°$ C. for about 0.5 to 2 hours. The equimolar amounts of the starting compounds are employed in general.

The thus obtained compound (I) can be easily separated and purified by the known method.

The third method

Specific examples of the compound represented by the formula (VI) may include, for example, the following compounds:
7-{2-[2-Amino-1,3-thiazol-4-yl]-2-[1-(3-(3,4-dihydroxybenzoyl)carbazoyl)-1-methylethoxyimino]acetamide}-3-acetoxymethyl-3-cephem-4-carboxylic acid,
7-{2-[2-Amino-1,3-thiazol-4-yl]-2-[1-(3-(3,4-dihydroxybenzoyl)carbazoyl)ethoxyimino]acetamide}-3-acetoxymethyl-3-cephem-4-carboxylic acid,
7-{2-[2-Amino-1,3-thiazol-4-yl]-2-[(3-(3,4-dihydroxybenzoyl)carbazoyl)methoxyimino]acetamide}-3-acetoxymethyl-3-cephem-4-carboxylic acid,
7-{2-[2-Amino-1,3-thiazol-4-yl]-2-[1-(3-(3,4-dihydroxybenzoyl)carbazoyl)-1-methylethoxyimino]acetamide}-3-chloromethyl-3-cephem-4-carboxylic acid,
7-{2-[2-Amino-1,3-thiazol-4-yl]-2-[1-(3-(3,4-dihydroxybenzoyl)carbazoyl)ethoxyimino]acetamide}-3-chloromethyl-3-cephem-4-carboxylic acid,
7-{2-[2-Amino-1,3-thiazol-4-yl]-2-[(3-(3,4-dihydroxybenzoyl)carbazoyl)methoxyimino]acetamide}-3-chloromethyl-3-cephem-4-carboxylic acid.

The compounds represented by the formula (VII) may include, for example, the following compounds:
7-Mercaptopyrazolo[1,5-a]pyrimidine,
3-Carboxy-7-mercaptopyrazolo[1,5-a]pyrimidine,
3-Carboxy-7-mercapto-5-methylpyrazolo[1,5-a]pyrimidine,
3-Carboxy-7-mercapto-5,6-dimethylpyrazolo[1,5-a]pyrimidine,
3-Carboxy-6,7-dihydro-8-mercapto-5H-cyclopenta[f]pyrazolo[1,5-a]pyrimidine,
7-Mercapto-s-triazolo[1,5-a]pyrimidine,
7-Mercapto-5-methyl-s-triazolo[1,5-a]pyrimidine,
2-Carboxy-7-mercapto-s-triazolo[1,5-a]pyrimidine,
2-Cyclopentyl-7-mercapto-s-triazolo[1,5-a]pyrimidine,
2-Carboxy-7-mercapto-5-methyl-s-triazolo[1,5-a]pyrimidine,
5-Carboxy-7-mercapto-2-methyl-s-triazolo[1,5-a]pyrimidine,
7-Mercapto-5,6-dimethyl-s-triazolo[1,5-a]pyrimidine,
5-Carboxy-2-ethyl-7-mercapto-s-triazolo[1,5-a]pyrimidine,
5-Carboxy-2-cyclopentyl-7-mercapto-s-triazolo[1,5-a]pyrimidine,
5-Carboxy-7-mercapto-2-trifluoromethyl-s-triazolo[1,5-a]pyrimidine,
2-Carboxy-7-mercapto-5,6-dimethyl-s-triazolo[1,5-a]pyrimidine,
7-Mercapto-5,6-dimethyl-2-trifluoromethyl-s-triazolo[1,5-a]pyrimidine,
6,7-Dihydro-8-mercapto-5H-cyclopenta[f]-s-triazolo[1,5-a]pyrimidine,
2-Carboxy-6,7-dihydro-8-mercapto-5H-cyclopenta[f]-s-triazolo[1,5-a]pyrimidine,
6,7-Dihydro-8-mercapto-2-methyl-5H-cyclopenta[f]-s-triazolo[1,5-a]pyrimidine,
6,7-Dihydro-8-mercapto-2-trifluoromethyl-5H-cyclopenta[f]-s-triazolo[1,5-a]pyrimidine,
5,6,7,8-Tetrahydro-9-mercapto-s-triazolo[5,1-b]quinazoline,
5,6,7,8-Tetrahydro-9-mercapto-2-methyl-s-triazolo[5,1-b]quinazoline,
5,6,7,8-Tetrahydro-9-mercapto-2-trifluoromethyl-s-triazolo[5,1-b]quinazoline,
2-Carboxy-5,6,7,8-tetrahydro-9-mercapto-s-triazolo[5,1-b]quinazoline,
7-Mercapto-5-methyltetrazolo[1,5-a]pyrimidine,
5-Carboxy-7-mercapto-2-methylpyrazolo[1,5-a]pyrimidine,
3-Carboxy-7-mercapto-5-trifluoromethylpyrazolo[1,5-a]pyrimidine,
3,5-Dicarboxy-7-mercaptopyrazolo[1,5-a]pyrimidine,
2,5-Dimethyl-7-mercaptopyrazolo[1,5-a]pyrimidine,
3,5-Dimethyl-7-mercaptopyrazolo[1,5-a]pyrimidine,
3-Carboxy-9-mercapto-5,6,7,8-tetrahydropyrazolo[5,1-b]quinazoline,
6-Carboxy-7-mercapto-s-triazolo[1,5-a]pyrimidine,
6-Carboxy-7-mercapto-2-methyl-s-triazolo[1,5-a]pyrimidine,
6-Carboxy-7-mercapto-2-trifluoromethyl-s-triazolo[1,5-a]pyrimidine, 6-Carboxy-2-cyclopentyl-7-mercapto-s-triazolo[1,5-a]pyrimidine, 5-Monofluoromethyl-7-mercapto-s-triazolo[1,5-a]pyrimidine, 2-Carboxy-5-monofluoromethyl-7-mercapto-s-triazolo[1,5-a]pyrimidine, 5-Carboxy-2-monofluoromethyl-7-mercapto-s-triazolo[1,5 a]pyrimidine.

The reaction of the compound (VI) and the compound (VII), is carried out by contacting them in water or water and a water-soluble organic solvent such as acetone, methanol, ethanol, isopropanol, acetonitrile, etc. When —COOM is a free carboxylic acid or its salt. This reaction is desirably carried out at around neutral of pH and the reaction system can be maintained at around neutral by properly adding alkaline compounds such as an alkali hydroxide, an alkali carbonate, an alkali hydrogencarbonate, an alkali dihydrogenphosphate, an alkali monohydrogenphosphate, etc. The reaction temperature is generally about 20° to 70° C. The terminal point of the reaction is confirmed by a thin layer chromatography. The reaction time is about 0.5 to 24 hours. Since the thus obtained compound (I') is being dissolved as a water-soluble alkali salt in a reaction mixture, an adsorption, separation and purification are carried out by using adsorptive resins such as Diaion HP-20 (trade name, produced by Mitsubishi Kasei Co.), Amberlite XAD II (trade name, produced by Rohm & Haas, Co.) etc.

In case of —COOM being ester, the reaction is carried out in an organic solvent such as methanol, ethanol, isopropanol, tetrahydrofuran, acetonitrile, dimethylformamide and the like at 50° to 100° C for 0.5 to 3 hours.

In the method of the present invention, the equimolar amounts of the compound (VI) and the compound (VII) are generally employed, respectively.

In the present invention, the compound represented by the formula (I) or its pharmaceutically acceptable salt can also be prepared by reacting a compound represented by the formula (XI):

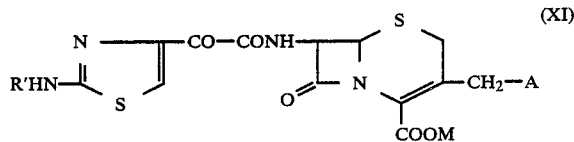

wherein R' and A are the same meanings as defined above, with the compound represented by the formula (XII):

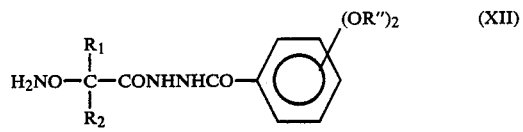

wherein $R_1$ and $R_2$ have the same meanings as defined above, or with a salt thereof.

The reaction involving compounds of the formula (XI) is preferably carried out by using a salt of the compound of the formula (XII). As such salts, preferably salts with mineral acids are employed, e.g., the hydrochlorides, or an organic sulfonate, e.g., the p-toluene sulfonates. The salt is preferably employed in about equimolar amounts up to slight excess thereof. The reaction is preferably carried out in a polar organic solvent, e.g., dimethylformamide, N-methylpyrrolidone, dimethylsulfoxide, acetonitrile, water or, particularly preferred, in dimethylacetamide. When using this latter solvent particularly high amounts of the syn form of the end products are obtained. The temperature of the reaction preferably lies in the range between 0° C. and room temperature.

In the present invention, the compound (I) obtained by each methods of (1), (2), and (3) as mentioned above can be converted into, if necessary, a pharmaceutically acceptable salt or an ester which is easily hydrolyzed in a human body when the compound has a free carboxylic acid.

The β-lactam compound according to the present invention can be administrated orally or non-orally to human beings or animals by various known administrating method.

Further, said compounds are used singly or by formulating with auxiliaries, liquid diluents, binders, lubricants, humectants, etc., which are pharmaceutically acceptable in general, for example, in the form of general medicinal compositions such as tablets, granulars, sugar coating tablets, powder, capsules, gels, dry syrup, syrup, amples, suspension, liquid, emulsion, ointments, paste, cream, suppositories, etc.

Moreover, as the other additives which can be formulated, there may be mentioned dissolution delaying agents, adsorption accelerating agents, surface active agents, etc. Any way, any forms which are pharmaceutically acceptable can be employed.

The β-lactam compound according to the present invention can be used as alone or mixture of two or more different kinds of derivatives and the amount of the compounds is about 0.1 to 99.5%, preferably 0.5 to 95% based on the weight of the all medicinal composition.

The medicinal composition containing the compound of the present invention can be formulated with an other compounds which are pharmaceutically active as effective ingredients other than said compound or mixtures thereof.

A dosage per day to a patient of the novel β-lactam compound according to the present invention may be varied depending upon an individual man, kinds of animals, weights thereof and a state to be remedied, but generally is in the range of 1 to 1000 mg per 1 kg of weight, preferably about 10 to 800 mg.

Thus, the compound of the above formula (I) obtained according to the present invention has high antibacterial activity as well as no toxicity at an effective dosage $LD_{50}$ value is 2 g/kg when intraveneous administration to mouse is carried out) and thus it is an effective compound as a medicine. For example, it shows excellent antibacterial activity against a wide range of pathogenic bacteria such as gram negative bacteria including *Pseudomonas aeruginosa* and gram positive bacteria. Also, the compound of the present invention is effective to a part of the third aged cephalosporin resistance acquired strains when administration thereof is carried out.

Accordingly, the β-lactam compound according to the present invention can be effectively utilized for the sake of prevention or remedy of diseases due to the aforesaid pathogenic bacteria in human beings or animals.

In the following, the present invention is explained in detail by referring to Examples.

EXAMPLE 1

Synthesis of
7-{2-[2-amino-1,3-thiazol-4-yl]-2-[1-(3-(3,4-dihydroxybenzoyl)carbazoyl)-1-methylethoxyimino]acetamide}-3-carbamoyloxymethyl-3-cephem-4-carboxylic acid.hydrochloride I. 5.45 g (11 mole) of 2-(2-amino-1,3-thiazol-4-yl)-2-}1-[3-(3,4-dihydroxybenzoyl)carbazoyl]-1-methylethoxyimino}acetic acid.hydrochloride, 4.83 g (11 mmole) of 7-amino-3 carbamoyloxymethyl-3-cephem-4-carboxylic acid diphenylmethyl ester and 2.02 g (13.2 mmole) of 1-hydroxybenzotriazole were dissolved in 40 ml of DMF, followed by ice-cooling and 2.72 g (13.2 mmole) of DCC was added thereto. The mixture was stirred for 30 minutes under ice-cooling and further stirred at room temperature for 1 hour. After filtration of the reaction mixture, the same amount of chloroform was added thereto and the mixture obtained was added dropwise into 2 liter of ether while vigorously stirring. The precipitates were collected by filtration, washed with ether and then dried to obtain 4.88 g of the desired diphenylmethyl ester (Yield: 50.3%).

II. To an ice-cooled mixture comprising 30 ml of trifluoroacetic acid and 7.5 ml of anisole, 4.88 g of diphenylmethyl ester obtained above was added and stirred for 30 minutes. The mixture obtained was added dropwise into 500 ml of ether while vigorously stirring. The precipitates were collected by filtration, washed with ether and dried to obtain 3.49 g of the title compound (Yield: 88.1%).

1H NMR (d$_6$-DMSO) δ:
1.58 (s, 6H), 3.72 (broad s, 2H), 4.88 (m, 2H),
5.33 (d, 1H), 5.87 - 6.18 (m, 1H), 6.83–7.65 (m, 4H).

3.29 g of hydrochloride thus obtained was suspended in 200 ml of water and the suspension was dissolved at pH 7.5 by adding 5% sodium bicarbonate solution. The mixture obtained was adsorbed to a column charged with 200 ml of HP-20 (trade name, produced by Mitsubishi Kasei Co.) and filled up with water, and then washed with water. Then, the title compound was eluted by 50% methanol - water and after evaporation of methanol, lyophilized to obtain 2.1 g of the desired sodium salt.

EXAMPLE 2

Synthesis of
7-{2-[2-amino-1,3-thiazol-4-yl]-2-[1-(3-(3,4-dihydroxybenzoyl)carbazoyl)-1-methylethoxyimino)acetamide}-3-[(2-carboxy-5-methyl-s-triazolo[1,5-a]pyrimidin-7-yl)thiomethyl-3-cephem-4-carboxylic acid.hydrochloride I. 4.95 g (10 mmole) of 2-(2-amino-1,3-thiazol-4-yl)-2-{1-[3-(3,4-dihydroxybenzoyl)carbazoyl]-1-methylethoxyimino}acetic acid.hydrochloride, 7.55 g (10 mmole) of 7-amino-3-[(2-carboxy-5-methyl-s-triazolo[1,5-a]pyrimidin-7-thiomethyl]-3-cephem-4-carboxylic acid diphenylmethyl ester and 1.84 g (12 mmole) of 1-hydroxybenzotriazole were dissolved in 40 ml of DMF, followed by ice-cooling and 2.48 g of (12 mmole) of DCC was added thereto. The mixture was stirred for 30 minutes under ice-cooling and further stirred at room temperature for 1 hour. After filtration of the reaction mixture, the same amount of chloroform was added thereto and the mixture obtained was added dropwise into 2 liter of ether while vigorously stirring. The precipitates were collected by filtration, washed with ether and then dried to obtain 9.62 g of the desired diphenylmethyl ester (Yield: 78%).

II. To an ice-cooled mixture comprising 30 ml of trifluoroacetic acid and 7.5 ml of anisole, 9.62 g of diphenylmethyl ester obtained above was added and stirred for 30 minutes. The mixture obtained was added dropwise into 500 ml of ether while vigorously stirring. The precipitates were collected by filtration, washed with ether and dried to obtain 4.48 g of the title compound (Yield: 67.4%).

$^1$H NMR (d$_6$-DMSO) δ:
1.57 (s, 6H), 2.52 (s, 3H), 3.75 (m, 2H), 4.55 (m, 2H), 5.26 (d, 1H), 5.78–6.15 (m, 1H), 6.85–7.68 (m, 5H).

4.28 g of hydrochloride thus obtained was suspended in 300 ml of water and the suspension was dissolved at pH 7 by adding 5% sodium bicarbonate solution and then the pH was adjusted to 5 with addition of 2N hydrochloric acid. The mixture obtained was adsorbed to a column charged with 300 ml of HP-20 and filled up with water, and then washed with water. Then, the title compound was eluted by 50% methanol-water and after evaporation of methanol, lyophilized to obtain 3.1 g of the desired sodium salt.

TEST EXAMPLE 1

20 mg/kg of the compound obtained in Example 1 was administered parenterally to Macaco and a central distribution volume and a tissue distribution volume were calculated by their concentrations in blood measured with time. The results are shown in Table 1.

The concentration of the compound was measured according to HPLC method. Microbondapack C18 (trade name, produced by Waters Co.) was used as a column and 8% acetonitrile-2% tetrahydrofuran-0.2% phosphoric acid was used as a solvent.

TABLE 1

| Compound | Central distribution volume (ml/kg) | Tissue distribution volume (ml/kg) |
|---|---|---|
| Compound obtained in Example 1 (Sodium salt) | 144.2 | 294.9 |

TEST EXAMPLE 2

The minimum inhibition concentrations (MIC) of the compounds obtained in Example 1 and Example 2 were measured according to the standard method of Japanese Chemotherapy Association. The results are shown in Table 2 and Table 3.

TABLE 2

| Strain | Compound to be tested | MIC (μg/ml) Compound obtained in Example 1 (Sodium salt) | Compound obtained in Example 2 (Sodium salt) | Compound obtained in Example 12 (Sodium salt) |
|---|---|---|---|---|
| S. aureus | 209P JC-1 | 3.13 | 3.13 | 0.39 |
|  | Smith | 6.26 | 6.25 | 0.78 |

TABLE 2-continued

| | | MIC (μg/ml) | | |
| | | Compound obtained in Example 1 (Sodium salt) | Compound obtained in Example 2 (Sodium salt) | Compound obtained in Example 12 (Sodium salt) |
| Strain | Compound to be tested | | | |
|---|---|---|---|---|
| E. coli | NIHJ JC-2 | 0.1 | 0.1 | 0.1 |
| | ML4707 | 0.025 | 0.01 | 0.012 |
| | GN5482 | 1.56 | 0.1 | 0.1 |
| K. pneumoniae | 4at521 | 0.012 | 0.012 | 0.012 |
| E. colacae | GN7471 | 25 | 6.25 | 3.13 |
| | 908RN | >100 | 1.56 | 3.13 |
| C. freundii | GN7391 | >100 | 12.5 | 12.5 |
| S. marcescens | GN10857 | 0.78 | 0.2 | 1.56 |
| P. vulgaris | GN7919 | 3.13 | 0.78 | 0.78 |
| P. aeruginosa | GN10362 | 0.05 | 0.2 | 0.1 |
| | 4au542 | 0.05 | 0.2 | 0.1 |
| | 5D58-1 | 0.2 | 0.39 | 0.1 |
| P. cepacia | OF189 | 0.025 | <0.006 | 0.025 |
| P. maltophilia | OF247 | 0.78 | 0.2 | 0.78 |
| A. xylosoxidans | OF1001 | 1.56 | 0.78 | 0.78 |
| A. calcoaceticu | OF1063 | 3.13 | 3.13 | 12.5 |

As is apparent from Table 2, the compounds of the present invention are effective to gram positive bacteria and gram negative bacteria and have wide range of antibacterial spectrum.

TABLE 3

| | | MIC (μg/ml) | | |
| | | Compound obtained in Example 1 (Sodium salt) | Compound obtained in Example 2 (Sodium salt) | Compound obtained in Example 12 (Sodium salt) |
| Strain | Compound to be tested | | | |
|---|---|---|---|---|
| E. cloacae | 5D52-2 | 25 | 0.20 | 0.20 |
| | 5D63-2 | 50 | 0.78 | 3.13 |
| | 1V25 | 50 | 6.25 | 12.5 |
| | 1Y247 | >100 | 6.25 | 25 |
| | 908RN | >100 | 3.13 | 3.13 |
| C. freundii | 5D60-1 | 50 | 1.56 | 3.13 |
| | 1R523 | 25 | 1.56 | 0.78 |
| | 1R524 | 12.5 | 0.78 | 0.78 |
| | 1R526 | 25 | 0.78 | 1.56 |
| | 1R527 | 12.5 | 0.78 | 0.78 |
| | 1U589 | 12.5 | 0.78 | 1.56 |
| | 1U692 | 25 | 1.56 | 3.13 |
| | GN7391 | >100 | 12.5 | 25 |

EXAMPLES 3 to 12

In the same manner as in Example 1 or 2, the following β-lactam compounds were synthesized. The results are shown in Table 4.

EXAMPLE 3

7-{2-[2-Amino-1,3-thiazol-4-yl]-2-[(3-(3,4-dihydroxybenzoyl)carbazoyl)methoxyimino]acetamide}-3-carbamoyloxymethyl-3-cephem-4-carboxylic acid.hydrochloride

EXAMPLE 4

7-{2-[2-Amino-1,3-thiazol-4-yl]-2-[1-(3-(3,4-dihydroxybenzoyl)carbazoyl)ethoxyimino]acetamide-3-carbamoyloxymethyl-3-cephem-4-carboxylic acid.hydrochloride

EXAMPLE 5

7-{2-[2-Amino-1,3-thiazol-4-yl]-2-[(3-(3,4-dihydroxybenzoyl)carbazoyl)methoxyimino]acetamide}-3-methylaminocarbonyloxymethyl-3-cephem-4-carboxylic acid.hydrochloride

EXAMPLE 6

7-{2-[2-Amino-1,3-thiazol-4-yl]-2-11-(3-(3,4-dihydroxybenzoyl)carbazoyl)ethoxyimino]acetamide}-3-methylaminocarbonyloxymethyl-3-cephem-4-carboxylic acid.hydrochloride

EXAMPLE 7

7-{2-[2-Amino-1,3-thiazol-4-yl]-2-[1-(3-(3,4-dihydroxybenzoyl)carbazoyl)-1-methylethoxyimino]acetamide}-3-methylaminocarbonyloxymethyl-3-cephem-4-carboxylic acid.hydrochloride

EXAMPLE 8

7-{2-[2-Amino-1,3-thiazol-4-yl]-2-[(3-(3,4-dihydroxybenzoyl)carbazoyl)methoxyimino]acetamide}-3-[(2-carboxy-5-methyl-s-triazolo[1,5-a]-pyrimidin-7-yl)thiomethyl]-3-cephem-4-carboxylic acid.hydrochloride

EXAMPLE 9

7-{2-[2-Amino-1,3-thiazol-4-yl]-2-[1-(3-(3,4-dihydroxybenzoyl)carbazoyl)ethoxyimino)acetamide}-3-[(2-carboxy-5-methyl-s-triazolo[1,5-a]-pyrimidin-7-yl)thiomethyl]-3-cephem-4-carboxylic acid.hydrochloride

EXAMPLE 10
7-{2-[2-Amino-1,3-thiazol-4-yl]-2-[(3-(3,4-dihydroxybenzoyl)carbazoyl)methoxyimino]acetamide}-3-[(5-methyl-s-triazolo[1,5-a]pyrimidin-7-yl)thiomethyl]-3-cephem-4-carboxylic acid.hydrochloride

EXAMPLE 11
7-{2-[2-Amino-1,3-thiazol-4-yl]-2-[1-(3-(3,4-dihydroxybenzoyl)carbazoyl)ethoxyimino]acetamide}-3-[(5-methyl-s-triazolo[1,5-a]pyrimidin-7-yl)thiomethyl]-3-cephem-4-carboxylic acid.hydrochloride

EXAMPLE 12
7-{2-[2-Amino-1,3-thiazol-4-yl]-2-[1-(3-(3,4-dihydroxybenzoyl)carbazoyl)-1-methylethoxyimino]acetamide}-3-[(5-methyl-s-triazolo[1,5-a]-pyrimidin-7-yl)thiomethyl]-3-cephem-4-carboxylic acid.hydrochloride

TABLE 4

| Example | Yield (%) | $^1$H NMR (d$_6$-DMSO) δ |
| --- | --- | --- |
| 3 | 44.3 | 3.73 (broad s, 2H), 4.35 (m, 2H), 4.70 (broad s, 2H), 5.18 (d, 1H), 5.58–5.87 (m, 1H), 6.58–7.46 (m, 4H) |
| 4 | 43.6 | 1.44 (d, 3H), 3.68 (broad s, 2H), 4.74 (broad s, 2H), 4.95 (q, 1H), 5.14 (d, 1H), 5.56–5.88 (m, 1H), 6.62–7.48 (m, 4H) |
| 5 | 52.4 | 2.70 (d, 3H), 3.73 (broad s, 2H), 4.38 (m, 2H), 4.84 (m, 2H), 5.23 (d, 1H), 5.62–6.03 (m, 1H), 6.62–7.55 (m, 4H) |
| 6 | 61.3 | 1.46 (d, 3H), 2.70 (d, 3H), 3.70 (broad s, 2H), 4.78 (m, 2H), 4.95 (q, 1H), 5.25 (d, 1H), 5.72–6.13 (m, 1H), 6.47–7.60 (m, 4H) |
| 7 | 58.6 | 1.60 (s, 6H), 2.68 (d, 3H), 3.75 (broad s, 2H), 4.92 (m, 2H), 5.30 (d, 1H), 5.82–6.15 (m, 1H), 6.80–7.63 (m, 4H) |
| 8 | 4.93 | 2.73 (s, 3H), 3.48 (broad s, 2H), 4.32 (m, 2H), 4.68 (m, 2H), 5.40 (d, 1H), 5.82–6.24 (m, 1H), 6.83–7.70 (m, 5H) |
| 9 | 53.8 | 1.44 (d, 3H), 2.75 (s, 3H), 3.78 (broad s, 2H), 4.62 (m, 2H), 5.38 (d, 1H), 4.94 (q, 1H), 5.80–6.26 (m, 1H), 6.78–7.46 (m, 5H) |
| 10 | 61.3 | 2.74 (s, 3H), 3.83 (broad s, 2H), 4.36 (m, 2H), 4.68 (m, 2H), 5.38 (d, 1H), 5.82–6.24 (m, 1H), 6.82–7.70 (m, 5H), 8.66 (s, 1H) |
| 11 | 63.5 | 1.46 (d, 3H), 2.76 (s, 3H), 3.72 (broad s, 2H), 4.58 (m, 2H), 4.96 (q, 1H), 5.39 (d, 1H), 5.82–6.20 (m, 1H), 6.82–7.72 (m, 5H), 8.68 (s, 1H) |
| 12 | 59.3 | 1.62 (s, 6H), 2.74 (s, 3H), 3.82 (s, 2H), 4.59 (m, 2H), 5.38 (d, 1H), 5.79–6.17 (m, 1H), 6.84–7.68 (m, 5H), 8.68 (s, 1H) |

EXAMPLE 13

Synthesis of 3-carboxy-7-mercapto-5-methylpyrazolo[1,5-a]pyrimidine

To a solution of 19 g of sodium hydrosulfide dissolved in 2 liter of water, 19 g (79 mmole) of 7-chloro-3-ethoxycarbonyl-5-methylpyrazolo[1,5-a]pyrimidine was added and stirred at 60° C. for 1 hour. The pH of the mixture was adjusted to about 2 with 2N hydrochloric acid under ice-cooling and stirring and the crystals precipitated were collected by filtration and washed with water. The crystals obtained were added to a solution containing 20 g of potassium hydroxide and 150 ml of water and stirred at 60° C. for 2 hours. Then, the pH thereof was adjusted to about 2 with 6N hydrochloric acid under ice-cooling and stirring and the crystals precipitated were collected by filtration. The crystals obtained were washed with water and then dried to obtain 15.8 g of the title compound (Yield: 95.6%).

$^1$H NMR (d$_6$-DMSO) δ:
2.48 (s, 3H), 6.95 (s, 1H), 8.50 (s, 1H).

EXAMPLES 14 to 16

In the same manner as in Example 13, the following compounds were synthesized.

EXAMPLE 14

3-Carboxy-7-mercaptopyrazolo[1,5-a]pyrimidine $^1$H NMR (d$_6$-DMSO) δ:
7.01 (d, J=7Hz, 1H), 7.80 (d, J=7Hz, 1H), 8.55 (s, 1H).

EXAMPLE 15

3-Carboxy-7-mercapto-5,6-dimethylpyrazolo[1,5-a]pyrimidine $^1$H NMR (d$_6$-DMSO) δ:
2.38 (s, 3H), 2.57 (s, 3H), 8.55 (s, 1H).

EXAMPLE 16

3-Carboxy-6,7-dihydro-8-mercapto-5H-cyclopenta[f]pyrazolo[1,5-a]pyrimidine $^1$H NMR (d$_6$-DMSO) δ:
1.92–2.45 (m, 2H), 2.75–3.38 (m, 4H), 8.45 (s, 1H).

EXAMPLE 17

Synthesis of 7-amino-3-[(3-carboxy-5-methylpyrazolo[1,5a]pyrimidin-7-yl)thiomethyl]-3-cephem-4-carboxylic acid To a suspension of 17.3 g (82.7 mmole) of 3-carboxy-5-methyl-7-mercaptopyrazolo[1,5-a]pyrimidine, 24.5 g (90 mmole) of 7-ACA and 200 ml of acetonitrile, 34 ml (0.27 mmole) of boron trifluoride ethyl ether complex was added and stirred at 50° C. for 2 hours. The reaction mixture was ice-cooled and then poured into 400 ml of water. The pH of the mixture was adjusted to about 2 with concentrated ammonia water and the crystals precipitated were collected by filtration and washed with water, acetone and then ether, followed by drying, to obtain 21.3 g of the title compound (Yield: 61%).

$^1$H NMR (CF$_3$COOD) δ:
2.52 (s 3H) 3.38 (s 2H) 4.44 (ABq J=8Hz, 14Hz, 2H), 4.98 (s, 2H), 7.20 (s, 1H), 8.45 (s, 1H).

EXAMPLES 18 to 20

In the same manner as in Example 17, the following compounds were synthesized.

EXAMPLE 18

7-Amino-3-[(3-carboxypyrazolo[1,5-a]pyrimidin-7-yl)thiomethyl]-3-cephem-4-carboxylic acid $^1$H NMR (CF$_3$COOD) δ:
3.92 (bs, 2H), 5.02 (ABq, J=12Hz, 13Hz, 2H), 5.53 (s, 2H), 7.93 (d, J=7Hz, 1H), 9.01 (d, J=7Hz, 1H), 9.06 (s, 1H).

EXAMPLE 19

7-Amino-3-[(3-carboxy-5,6-dimethylpyrazolo[1,5-a]pyrimidin-7-yl)thiomethyl[-3-cephem-4-carboxylic acid $^1$H NMR (CF$_3$COOD) δ:
2.68 (s, 3H), 3.07 (s, 3H), 3.90 (bs, 2H), 5.28–5.56 (m, 4H), 8.96 (s, 1H).

EXAMPLE 20

7-Amino-3-[(3 carboxy-6,7-dihydro-5H-cyclopenta[f]pyrazolo[1,5-a]pyrimidin-8-yl)thiomethyl]-3-cephem-4-carboxylic acid $^1$H NMR (CF$_3$COOD) δ:
2.32–2.91 (m, 2H), 3.08–3.63 (m, 4H), 3.98 (bs, 2H), 5.33–5.64 (m, 4H), 8.97 (s, 1H).

EXAMPLE 21

Synthesis of 7-amino-3-[(3-carboxy-5-methylpyrazolo[1,5-a]pyrimidin-7-thiomethyl-3-cephem-4-carboxylic acid diphenylmethyl ester To a suspension of 21.2 g (50.3 mmole) of 7-amino-3-[(3-carboxy-5-methylpyrazolo[1,5-a]pyrimidin-7-yl)thiomethyl]-3-cephem-4-carboxylic acid, 150 ml of methanol and 450 ml of methylene chloride, diphenyl diazomethane synthesized from 29.4 g (0.15 mole) of benzophenone hydrazone, 32.5 g (0.15 mole) of mercuric oxide (yellow) and 200 ml of n-hexane and dissolved in 50 ml of methylene chloride was added dropwise over 1 hour and stirred at room temperature for 12 hours.

The reaction mixture was concentrated and then crystallized with addition of ether. The crystals obtained were collected by filtration and dried to obtain 31.71 g of the title compound (Yield: 83.6%).

$^1$H NMR (d$_6$-DMSO) δ:
2.57 (s, 3H), 3.38 (s, 2H), 4.27 (bs, 2H), 4.87 (d, 1H), 5.03 (d, 1H), 6.72 (s, 1H), 7.18 (s, 1H), 7.28–7.85

(m, 22H), 8.80 (s, 1H).

EXAMPLES 22 to 24

In the same manner as in Example 21, the following compounds were synthesized.

EXAMPLE 22

7-Amino-3-[(3-carboxypyrazolo[1,5-a]pyrimidin-7-yl)thiomethyl]-3-cephem-4-carboxylic acid diphenylmethyl ester $^1$H NMR (d$_6$-DMSO) δ:
3.69 (bs, 2H), 4.30 (bs, 2H), 4.92 (d, J=5Hz, 1H), 5.11 (d, J=5Hz, 1H), 6.98–7.81 (m, 23H), 8.63 (d, J=5Hz, 1H), 8.83 (s, 1H).

EXAMPLE 23

7-Amino-3-[(3-carboxy-5,6-dimethylpyrazolo[1,5-a]pyrimidin-7-yl)thiomethyl]-3-cephem-4-carboxylic acid diphenylmethyl ester $^1$H NMR d$_6$-DMSO) δ:
2.43 (s, 3H), 2.60 (s, 3H), 3.68 (bs, 2H), 4.32 (ABq, J=7Hz, 14Hz, 2H), 4.82–5.18 (m, 2H), 6.59 (s, 1H), 7.18–7.96 (m, 21H), 8.77 (s, 1H).

EXAMPLE 24

7-Amino-3-carboxy-6,7-dihydro-5H-cyclopenta[f]pyrazolo[1,5-a]pyrimidine-8-yl)thiomethyl]-3-cephem-4-carboxylic acid diphenylmethyl ester $^1$H NMR (d$_6$-DMSO) δ:
2.02–2.41 (m, 2H), 2.78–3.24 (m, 4H), 3.71 (bs, 2H), 4.41 (ABq, J=8Hz, 14Hz, 2H), 4.88 (d, J=6Hz, 1H), 5.08 (d, J=6Hz, 1H), 6.15 (s, 1H), 7.20–7.88 (m, 21H), 8.78 (s, 1H).

EXAMPLE 25

Synthesis of 7-{2-[2-amino-1,3-thiazol-4-yl]-2-[1-(3-(3,4-dihydroxybenzoyl)carbazoyl)-1-methylethoxyimino]acetamide}-3-[(3-carboxy-5-methylpyrazolo[1,5-a]pyrimidin-7-yl)thiomethyl]-3-cephem-4-carboxylic acid.hydrochloride I. 16 g (35 mmole) of 2-(2-amino-1,3-thiazol-4-yl)-2-{1-[3-(3,4-dihydroxybenzoyl)carbazoyl]-1-methylethoxyimino}acetic acid.hydrochloride, 31.6 g (42 mmole) of 7-amino-3-[(3-carboxy-5-methylpyrazolo[1,5-a]pyrimidin-7-yl)thiomethyl]-3-cephem-4-carboxylic acid diphenylmethyl ester and 6.43 g (42 mmole) of 1-hydroxybenzotriazole were dissolved in 100 ml of DMF, followed by ice-cooling and 8.7 g (42 mmole) of DCC was added thereto. The mixture was stirred for 30 minutes under ice-cooling and further stirred at room temperature for 1 hour.

After filtration of the reaction mixture, the same amount of chloroform was added thereto and the mixture obtained was added dropwise into 8 liters of ether while vigorously stirring. The precipitates were collected by filtration, washed with ether and then dried to obtain 41 g of the desired diphenylmethyl ester (Yield: 98%).

II. To an ice-cooled mixture comprising 100 ml of trifluoroacetic acid and 30 ml of anisole, 17.3 g (14.5 mmole) of diphenylmethyl ester obtained above was added and stirred for 30 minutes. The mixture obtained was added dropwise into 2 liters of ether while vigorously stirring. The precipitates were collected by filtration, washed with ether and dried to obtain 9.24 g of the title compound (Yield: 74%).

$^1$H NMR (d$_6$-DMSO) δ:
1.62 (s, 6H), 2.66 (s, 3H), 3.82 (s, 2H), 4.53 (bs, 2H), 5.40 (d, J=5Hz, 1H), 5.83–6.23 (m, 1H), 6.92–7.68

(m, 5H), 8.78 (s, 1H).

8.5 g of hydrochloride thus obtained was suspended in 500 ml of water and the suspension was dissolved at pH 7 by adding 5% sodium bicarbonate solution and then the pH was adjusted to 5 with 2N hydrochloric acid. The mixture obtained was adsorbed to a column charged with 300 ml of HP-20 and filled up with water, and then washed with water. Then, the title compound was eluted by 50% methanol-water and after evaporation of methanol, lyophilized to obtain 6.7 g of the desired sodium salt.

EXAMPLES 26 to 28

In the same manner as in Example 25, the following compounds were synthesized.

EXAMPLE 26

7-{2-[2-Amino-1,3-thiazol-4-yl]-2-[1-(3-(3,4-dihydroxybenzoyl)carbazoyl)-1-methylethoxyimino]acetamide}-3-[(3-carboxypyrazolo[1,5-a]pyrimidin-7-yl)thiomethyl]-3-cephem-4-carboxylic acid.hydrochloride $^1$H NMR (d$_6$-DMSO) δ:
1.58 (s, 6H), 3.82 (bs, 2H), 4.50 (bs, 2H), 5.38 (d, J=4Hz, 1H), 582–6.16 (m, 1H), 6.83–7.63 (m, 5H), 8.68–8.91 (m, 2H).

EXAMPLE 27

7-{2-[2-Amino-1,3-thiazol-4-yl]-2-[1-(3-(3,4-dihydroxybenzoyl)carbazoyl)-1-methylethoxyimino]acetamide}-3-[(3-carboxy-5,6-dimethylpyrazolo[1,5-a]pyrimidin-7-yl)thiomethyl]-3-cephem-4-carboxylic acid.hydrochloride $^1$H NMR (d$_6$-DMSO) δ:
1.60 (s, 6H), 2.50 (s, 3H), 2.62 (s, 3H), 3.80 (s, 2H), 4.48 (bs, 2H), 5.19 (d, J=4Hz, 1H), 5.72–6.14 (m, 1H), 6.82–7.63 (m, 4H), 8.67 (s, 1H).

EXAMPLE 28

7-{2-[2-Amino-1,3-thiazol-4-yl]-2-[1-(3-(3,4-dihydroxybenzoyl)carbazoyl)-1-methylethoxyimino]acetamide}-3-[(3-carboxy-6,7-dihydro-5H-cyclopenta[f]pyrazolo[1,5-a]pyrimidin-8-yl)thiomethyl]-3-cephem-4-carboxylic acid.hydrochloride $^1$H NMR (d$_6$-DMSO) δ:
1.61 (s, 6H), 2.02–2.48 (m, 2H), 2.83–3.42 (m, 4H), 3.84 (s, 2H), 4.50 (bs, 2H), 5.24 (d, J=5Hz, 1H), 5.82–6.14 (m, 1H), 6.87–7.64 (m, 4H), 8.68 (s, 1H).

SYNTHESIS EXAMPLE 1

Synthesis of 7-mercapto-5-methyltetrazolo[1,5-a]pyrimidine

I. Synthesis of 5-methyl-7-hydroxytetrazolo[1,5-a]pyrimidine

A mixture of 51.5 g (0.5 mole) of 5-aminotetrazole, 108 ml (1 mole) of methyl acetoacetate ester and 200 ml of acetic acid was stirred at 85° C. for 18 hours and ice-cooled. The precipitates were collected by filtration and washed with acetic acid and isopropanol, followed by drying, to obtain 57.91 g of the title compound (Yield: 42.6%).

$^1$H NMR (d$_6$-DMSO) δ:
2.65 and 2.67 (s, 3H), 6.36 and 6.38 (s, 1H).

II. Synthesis of 7-chloro-5-methyltetrazolo[1,5-a]pyrimidine

A mixture of 67.88 g (0.45 mole) of 5-methyl-7-hydroxytetrazolo[1,5-a]pyrimidine and 300 ml of phosphorus oxychloride was stirred for 1.5 hours in a bath of 100° C. and then concentrated. The residue obtained was dissolved in 600 ml of chloroform, ice-cooled and then washed with water, followed by drying over anhydrous magnesium sulfate to evaporate the solvent. The set residue was collected by filtration with addition of n-hexane and dried to obtain 70.2 g of the title compound (Yield: 92%).

$^1$H NMR (d$_6$-DMSO) δ:
2.58 and 3.07 (s, 3H), 7.47 and 7.82 (s, 1H).

III. Synthesis of 7-mercapto-5-methyltetrazolo[1,5-a]pyrimidine

To a solution of 108 g (1.35 mole) of sodium hydrosulfide dissolved in 4 liters of water, 70 g (0.41 mole) of 7-chloro-5-methyltetrazolo[1,5-a]pyrimidine was added and the mixture was heated to 60° C. and stirred for 2.5 hours. The pH of the mixture was adjusted to about 1 with 2N hydrochloric acid under ice-cooling and stirring. The precipitates were collected by filtration and washed with water, isopropanol and then ether, followed by drying, to obtain 64 g of the title compound (Yield: 93%).

$^1$H NMR (d$_6$-DMSO) δ:
2.60 and 2.62 (s, 3H), 7.05 and 7.08 (s, 1H).

SYNTHESIS EXAMPLE 2

Synthesis of 7-amino-3-[(5-methyltetrazolo[1,5-a]pyrimidin-7-yl)thiomethyl]-3-cephem-4-carboxylic acid To a suspension of 16.72 g (0.1 mole) of 7-mercapto-5-methyltetrazolo[1,5-a]pyrimidine, 27.2 g (0.1 mole) of 7-ACA and 200 ml of acetonitrile, 37 ml (0.3 mmole) of boron trifluoride ethyl ether complex was added and stirred at 50° C. for 2 hours.

The reaction mixture was ice-cooled and then poured into 400 ml of water. The pH of the mixture was adjusted to 2 with concentrated ammonia water and the crystals precipitated were collected by filtration and washed with water, acetone and then ether, followed by drying, to obtain 25 g of the title compound (Yield: 66%).

$^1$H NMR (CF$_3$COOD+D$_2$O) δ:
2.98 (s, 3H), 3.96 (bs, 2H), 4.78 (ABq, J=28HZ, 14Hz, 2H), 5.37 (s, 2H), 7.25 (s, 1H).

SYNTHESIS EXAMPLE 3

Synthesis of 7-amino-3-[(5-methyltetrazolo[1,5-a]pyrimidin-7-yl)thiomethyl]-3-cephem-4-carboxylic acid diphenylmethyl ester To a suspension of 25 g (0.066 mole) of 7-amino-3-[(5-methyltetrazolo[1,5-a]pyrimidin-7-yl)thiomethyl]-3-cephem-4-carboxylic acid, 100 ml of methanol and 300 ml of methylene chloride, diphenyl diazomethane synthesized from 39.25 g (0.2 mole) of benzophenone hydrazone, 43.3 g (0.2 mole) of mercuric oxide (yellow) and 300 ml of n-hexane and dissolved in 50 ml of methylene chloride was added dropwise over 3 hours and stirred at room temperature for 12 hours.

The residue obtained by filtration and subsequent concentration of the reaction mixture was crystallized with addition of isopropyl ether. The crystals obtained were collected by filtration and dried to obtain 13.9 g of the title compound (Yield: 38.6%).

$^1$H NMR (d$_6$-DMSO+CDCl$_3$) δ:
2.81 (s, 3H), 3.68 (bs, 2H), 4.38 (ABq, J=21Hz, 14Hz, 2H), 4.92–5.14 (m, 2H), 7.02–7.74 (m, 12H).

EXAMPLE 29

Synthesis of
7-{2-[2-amino-1,3-thiazol-4-yl]-2-[1-(3-(3,4-dihydroxybenzoyl)carbazoyl)-1-methylethoxyimino]acetamide}-3-[(5-methyltetrazolo[1,5-a]pyrimidin-7-yl)thiomethyl]-3-cephem-4-carboxylic acid.hydrochloride I. 10.1 g (22 mmole) of 2-(2-amino-1,3-thiazol-4-yl)-2-{1-[3-(3,4-dihydroxybenzoyl)carbazoyl]-1-methylethoxyimino}acetic acid.hydrochloride, 13.9 g (25 mmole) of 7-amino-3-[(5-methyltetrazolo[1,5-a]pyrimidin-7-yl)thiomethyl]-3-cephem-4-carboxylic acid diphenylmethyl ester and 3.83 g (25 mmole) of 1-hydroxybenzotriazole were dissolved in 60 ml of DMF, followed by ice-cooling and 5.78 g (28 mmole) of DCC was added thereto. The mixture was stirred for 30 minutes under ice-cooling and further stirred at room temperature of 1 hour.

After filtration of the reaction mixture, the same amount of chloroform was added thereto and the mixture obtained was added dropwise into 4 liter of ether while vigorously stirring. The precipitates were collected by filtration, washed with ether and then dried to obtain 20.3 g of the desired diphenylmethyl ester (Yield: 93.5%).

II. To an ice-cooled mixture comprising 40 ml of trifluoroacetic acid and 10 ml of anisole, 4.15 of diphenylmethyl ester obtained above was added and stirred for 30 minutes. The mixture obtained was added dropwise into 1 liter of ether while vigorously stirring. The precipitates were collected by filtration, washed with ether and dried to obtain 2.48 g of the title compound (Yield: 72%).

$^1$H NMR (d$_6$-DMSO) δ:
1.52 (s, 6H), 2.81 (s, 3H), 3.62 (bs, 2H), 4.11 (bs, 2H), 5.18 (d, J=5Hz, 1H), 5.72–6.02 (m, 1H), 6.83–7.68 (m, 5H).

EXAMPLE 30

Synthesis of
8-mercapto-2-methoxycarbonyl-6,7-dihydro-5H-cyclopenta[f]-s-triazolo[1,5-a]pyrimidine I. Synthesis of
8-hydroxy-2-methoxycarbonyl-6,7-dihydro-5H-cyclopenta[f]-s-triazolo[1,5-a]pyrimidine A mixture of 14.2 g (0.1 mole) of 3-amino-5-methoxycarbonyl-1,2,4-triazole, 34.3 ml (0.23 mole) of ethyl-2-oxocyclopentanecarboxylate and 150 ml of acetic acid was stirred under reflux for 6hours and then allowed to stand for cooling. The crystals precipitated were collected by filtration and washed with methanol and then ether, followed by drying, to obtain 17.8 g of the title compound (Yield: 76%).

$^1$H NMR (d$_6$-DMSO) δ:
1.98–2.44 (m, 2H), 2.57–3.23 (m, 4H), 3.98 (s, 3H).

II. Synthesis of
8-chloro-2-methoxycarbonyl-6,7-dihydro-5H-cyclopenta[f]-s-triazolo[1,5-a]pyrimidine To an ice-cooled mixture of 17.73 g (75.7 mole) of 8-hydroxy-2-methoxycarbonyl-6,7-dihydro-5H-cyclopenta[f]-s-triazolo[1,5-a]pyrimidine and 150 ml of phosphorus oxychloride, 9.6 ml (75.7 mmole) of N,N-dimethylaniline was added dropwise while stirring over 10 minutes and then stirred for 1.5 hours in a bath of 110° C.

The residue obtained by concentration of the mixture was dissolved in 300 ml of chloroform and ice-cooled, and while stirring, 100 g of finely crushed ice was added thereto, followed by stirring. After the finely crushed ice was dissolved, an organic layer was obtained and washed with water, followed by drying over anhydrous magnesium sulfate to evaporate the solvent. The residue crystallized was collected by filtration with addition of n-hexane and dried to obtain 18.6 g of the title compound (Yield: 97%).

$^1$H NMR (d$_6$-DMSO) δ:
2.12–2.58 (m, 2H), 2.98–3.38 (m, 4H), 4.01 (s, 3H).

III. Synthesis of
8-mercapto-2-methoxycarbonyl-6,7-dihydro-5H-cyclopenta[f]-s-triazolo[1,5-a]pyrimidine To a solution of 17.6 g of sodium hydrosulfide dissolved in 800 ml of water, 18.5 g (73.2 mmole) of 8-chloro-2-methoxycarbonyl-6,7-dihydro-5H-cyclopenta[f]-s-triazolo[1,5-a]pyrimidine was added and the mixture was stirred at room temperature for 30 minutes. The pH of the mixture was adjusted to about 2 with 2N hydrochloric acid under ice-cooling and stirring. The precipitates were collected by filtration and washed with water, isopropanol and then ether, followed by drying, to obtain 18.0 g of the title compound (Yield: 98%).

$^1$H NMR (d$_6$-DMSO) δ:
1.97–2.44 (m, 2H , 2.70–3.32 (m, 4H), 4.03 (s, 3H).

EXAMPLE 31

Synthesis of
2-carboxy-8-mercapto-6,7-dihydro-5H-cyclopenta[f]-s-triazolo[1,5-a]pyrimidine A suspension of 18.8 g (75 mmole) of 8-mercapto-2-methoxycarbonyl-6,7-dihydro-5H-cyclopenta[f]-s-triazolo[1,5-a]pyrimidine and 150 ml of a 2N aqueous sodium hydroxide solution was stirred at room temperature for 3 hours and the pH was adjusted to about 2 with 2N hydrochloric acid under ice-cooling and stirring. The precipitates were collected by filtration and washed with water, acetone and then ether, followed by drying, to obtain 17.49 g of the title compound (Yield: 98.7%).

$^1$H NMR (d$_6$-DMSO) δ:
1.98–2.42 (m, 2H), 2.68–3.24 (m, 4H).

EXAMPLE 32

Synthesis of
7-amino-3-[(2-carboxy-6,7-dihydro-5H-cyclopenta[f]-s-triazolo[1,5-a]pyrimidin-8-yl)thiomethyl-3-cephem-4-carboxylic acid To a suspension of 17.17 g (72.7 mmole) of 2-carboxy-8-mercapto-6,7-dihydro-5H-cyclopenta[f]-s-triazolo[1,5-a]pyrimidine, 19.8 g (72.7 mmole) of 7-ACA and 150 ml of acetonitrile, 26.8 ml (0.218 mole) of boron trifluoride ethyl ether complex was added and stirred at 50° C. for 2 hours.

The reaction mixture was ice-cooled and then poured into 400 ml of water. The pH of the mixture was adjusted to about 2.5 with concentrated ammonia water and the mixture was stirred for 1 hour. The precipitates were collected by filtration and washed with water, acetone and then ether, followed by drying, to obtain 16.27 g of the title compound (Yield: 49.9%).

$^1$H NMR (CF$_3$COOD) δ:
1.87–2.36 (m, 2H), 2.72–3.15 (m, 4H), 3.51 (s, 2H), 4.40 (ABq, J=16Hz, 2H), 4.97 (s, 2H).

EXAMPLE 33

Synthesis of 7-{2-[2-amino-1,3-thiazol-4-yl]-2-[1-(3-(3,4-dihydroxybenzoyl)carbazoyl)-1-methylethoxyimino]acetamide}-3-[(2-carboxy-6,7-dihydro-5H-cyclopenta[f]-s-triazolo[1,5-a]pyrimidin-8-yl)thiomethyl]-3-cephem-4-carboxylic acid.hydrochloride I. 11.5 g (25 mmole) of 2-(2-amino-1,3-thiazol-4-yl)-2-{1-[3-(3,4-dihydroxybenzoyl)carbazoyl]-1-methylethoxyimino}acetic acid.hydrochloride, 23.4 g (30 mmole) of 7-amino-3-[(2-carboxy-6,7-dihydro-5H-cyclopenta[f]-s-triazolo[1,5-a]pyrimidin-8-yl)thiomethyl]-3-cephem-4-carboxylic acid diphenylmethyl ester and 4.6 g (30 mmole) of 1-hydroxybenzotriazole were dissolved in 80 ml of DMF, followed by ice-cooling and 6.2 g of DCC was added thereto. The mixture was stirred for 30 minutes under ice-cooling and further stirred at room temperature for 1 hour.

After filtration of the reaction mixture, the same amount of chloroform was added thereto and the mixture was added into 5 liters of ether while vigorously stirred. The precipitates were collected by filtration and dried to obtain 29.3 g of diphenylmethyl ester (Yield: 96%).

II. To an ice-cooled mixture comprising 40 ml of trifluoroacetic acid and 15 ml of anisole, 6.5 g of diphenylmethyl ester obtained above was added and stirred for 30 minutes. The mixture obtained was added dropwise into 1 liter of ether while vigorously stirring. The precipitates were collected by filtration, washed with ether and dried to obtain 3.23 g of the title compound (Yield: 68.2%).

$^1$H NMR (d$_6$-DMSO) δ:
1.62 (s, 6H), 1.98–2.48 (m, 2H), 2.92–3.41 (m, 4H), 3.83 (s, 2H), 4.43 (bs, 2H), 5.31 (d, J=5Hz, 1H), 5.82–6.14 (m, 1H), 6.83–7.68 (m, 4H).

EXAMPLE 34

Synthesis of 8-mercapto-6,7-dihydro-5H-cyclopenta[f]-s-triazolo[1,5-a]pyrimidine I. Synthesis of 8-hydroxy-6,7-dihydro-5H-cyclopenta[f]-s-triazolo[1,5-a]pyrimidine A mixture of 8.4 g (0.1 mole) of 3-amino-1,2,4-triazole, 17.8 ml (0.12 mole) of ethyl-2-oxocyclopentanecarboxylate and 50 ml of acetic acid was stirred under reflux for 2 hours and then ice-cooled. The crystals precipitated were collected by filtration and washed with methanol and then ether, followed by drying, to obtain 13.28 g of the title compound (Yield: 75%).

$^1$H NMR (d$_6$-DMSO) δ:
2.01–2.47 (m, 2H), 2.61–3.22 (m, 4H), 8.31 (s, 1H).

II. Synthesis of 8-chloro-6,7-dihydro-5H-cyclopenta[f]-s-triazolo[1,5-a]pyrimidine A mixture of 13 g (73.8 mmole) of 8-hydroxy-6,7-dihydro-5H-cyclopenta[f]-s-triazolo[1,5-a]pyrimidine, and 50 ml of phosphorous oxychloride was stirred for 1.5 hours in a bath of 100° C. and then concentrated. The residue dissolved in 300 ml of chloroform was ice-cooled and while stirring, 100 g of finely crushed ice was added thereto, followed by stirring.

After the finely crushed ice was dissolved, the mixture was adjusted to about pH 2 with a 2N aqueous sodium hydroxide solution and stirred sufficiently to obtain an organic layer. The organic layer was washed with water, followed by drying over anhydrous magnesium sulfate to evaporate the solvent. The solidified residue was collected by filtration with addition of n-hexane and dried to obtain 13.6 g of the title compound (Yield: 95%).

$^1$H NMR (d$_6$-DMSO) δ:
2.08–2.58 (m, 2H), 2.96–3.38 (m, 4H), 8.77 (s, 1H).

III. Synthesis of 8-mercapto-6,7-dihydro-5H-cyclopenta[f]-s-triazolo[1,5-a]pyrimidine To a solution of 17.6 g (0.22 mole) of sodium hydrosulfide dissolved in 800 ml of water, 13.5 g (69 mmole) of 8-chloro-6,7-dihydro-5H-cyclopenta[f]-s-triazolo[1,5-a]pyrimidine was added and the mixture was stirred at 50° C. for 1 hour. After filtration, the pH of the mixture was adjusted to about 1 with 2N hydrochloric acid under ice-cooling and stirring. The precipitates were collected by filtration and washed with water, isopropanol and the ether, followed by drying, to obtain 12.98 g of the title compound (Yield: 97.9%).

$^1$H NMR (d$_6$-DMSO) δ:
1.94–2.47 (m, 2H), 2.65–3.19 (m, 4H), 8.69 (s, 1H).

EXAMPLE 35

Synthesis of 7-amino-3-[(6,7-dihydro-5H-cyclopenta[f]-s-triazolo[1,5-a]pyrimidin-8-yl)thiomethyl]-3-cephem-4-carboxylic acid To a suspension of 12.8 g (66.5 mmole) of 8-mercapto-6,7-dihydro-5H-cyclopenta[f]-s-triazolo[1,5pyrimidine, 18.1 g (66.5 mmole) of 7-ACA and 150 ml of acetonitrile, 25 ml (0.2 mole) of boron trifluoride ethyl ether complex was added and stirred at 50 ° C for 2 hours.

The reaction mixture was ice-cooled and then poured into 300 ml of water. The pH of the mixture was adjusted to about 2.5 with concentrated ammonia water and the crystals precipitated were collected by filtration and washed with water, acetone and then ether, followed by drying, to obtain 10.71 g of the title compound (Yield: 40%).

$^1$H NMR (CF$_3$COOD) δ:
2.24–2.78 (m, 2H), 3.21–3.68 (m, 4H), 3.92 (s, 2H), 4.96 (ABq, J=14Hz, 2H), 5.48 (s, 2H), 9.20 (s, 1H).

EXAMPLE 36

Synthesis of 7-{2-[2-amino-1,3-thiazol-4-yl]-2-[1-(3(3,4-dihydroxybenzoyl)carbazoyl)-1-methylethoxyimino]acetamide}-3-[(6,7-dihydro-5H-cyclopenta[f]-s-triazolo[1,5-a]pyrimidin-8-yl)thiomethyl[-3-cephem-4-carboxylic acid.hydrochloride I. 11.5 g (25 mmole) of 2-(2-amino-1,3-thiazol-4-yl)-2-{1-[3-(3,4-dihydroxybenzoyl)carbazoyl]-1-methylethoxyimino}acetic acid.hydrochloride, 14.8 g (25.9 mmole) of 7-amino-3-[6,7-dihydro-5H-cyclopenta[f]-s- triazolo[1,5-a]-pyrimidin-8-yl)thiomethyl]-3-cephem-4-carboxylic acid diphenylmethyl ester and 4.6 g (30 mmole) of 1-hydroxybenzotriazole were dissolved in 80 ml of DMF, followed by ice-cooling and 6.2 g of DCC was added thereto. The mixture was stirred for 30 minutes under ice-cooling and further stirred at room temperature for 1 hour.

After filtration of the reaction mixture, the same amount of chloroform was added thereto and the mixture obtained was added dropwise into 5 liter of ether while vigorously stirring. The precipitates were collected by filtration, washed with ether and then dried to obtain 24 g of the desired diphenylmethyl ester (Yield: 95%).

II. To an ice-cooled mixture comprising 60 ml of trifluoroacetic acid and 15 ml of anisole, 7.6 g of diphenylmethyl ester obtained above was added and stirred for 30 minutes. The mixture obtained was added dropwise into 1 liter of ether while vigorously stirring. The precipitates were collected by filtration, washed with ether and dried to obtain 4.1 g of the title compound (Yield: 64.6%).

$^1$H NMR (d$_6$-DMSO) δ:
1.61 (s, 6H), 1.96–2.38 (m, 2H), 2.98–3.36 (m, 4H), 3.82 (s, 2H), 4.43 (m, 2H), 5.28 (d, J=5Hz, 1H), 5.82–6.14 (m, 1H), 6.83–7.64 (m, 4H), 8.78 (s, 1H).

SYNTHESIS EXAMPLE 4

Synthesis of 7-mercapto-5-methoxycarbonyl-2-methyl-s-triazolo[1,5-a]pyrimidine

I. Synthesis of 7-chloro-5-methoxycarbonyl-2-methyl-s-triazolo[1,5-a]pyrimidine

To an ice-cooled mixture of 30.5 g (0.15 mole) of 7-hydroxy-5-methoxycarbonyl-2-methyl-s-triazolo[1,5-a]pyrimidine and 300 ml of phosphorus oxychloride, 18.6 ml (0.15 ml) of N,N-dimethylaniline was added dropwise over 5 minutes and the mixture was stirred under reflux for 1 hour, followed by concentration. The residue obtained was dissolved in 300 ml of chloroform and washed with water, followed by drying over anhydrous magnesium sulfate. The solvent was evaporated and n-hexane was added to the set residue. The crystals were collected by filtration and dried to obtain 11.19 g of the title compound (Yield: 33.7%).

$^1$H NMR (d$_6$-DMSO) δ:
2.64 (s, 3H), 4.03 (s, 3H), 8.18 (s, 1H).

II. Synthesis of 7-mercapto-5-methoxycarbonyl-2-methyl-s-triazolo[1,5-a]pyrimidine To a solution of 12 g (0.15 mole) of sodium hydrosulfide dissolved in 800 ml of water, 11 g (48.5 mmole) of 7-chloro-5-methoxycarbonyl-2-methyl-s-triazolo[1,5-a]pyrimidine was added and the mixture was stirred at room temperature for 40 minutes.

The pH of the mixture was adjusted to 2 with a 2N hydrochloric acid. The precipitates were collected by filtration and washed with water and then isopropanol, followed by drying, to obtain 7.77 g of the title compound (Yield: 71%).

$^1$H NMR (d$_6$-DMSO) δ:
2.60 (s, 3H), 3.98 (s, 3H), 7.65 (s, 1H).

SYNTHESIS EXAMPLE 5

Synthesis of 5-carboxy-7-mercapto-2-methyl-s-triazolo[1,5-a]pyrimidine

A mixture of 7.7 g (34 mmole) of 7-mercapto-5-methoxycarbonyl-2-methyl-s-triazolo[1,5-a]pyrimidine and 70 ml of a 2N NaOH was stirred at room temperature for 2 hours and then ice-cooled. The pH of the mixture was adjusted to 2 with 6N HCl. The precipitates were collected by filtration and washed with water and then acetone, followed by drying, to obtain 7.08 g of the title compound (Yield: 99%).

$^1$H NMR (d$_6$-DMSO) δ:
2.55 (s, 3H), 7.58 (s, 1H).

SYNTHESIS EXAMPLE 6

Synthesis of 7-amino-3-[(5-carboxy-2-methyl-s-triazolo[1,5-a]pyrimidin-7-yl)thiomethyl-3-cephem-4-carboxylic acid To a suspension of 7.0 g (33.3 mmole) of 5-carboxy 7-mercapto-2-methyl-s-triazolo[1,5-a]pyrimidine, 9.07 g (33.3 mmole) of 7-ACA and 150 ml of acetonitrile, 12.3 ml (100 mmole) of boron trifluoride ethyl ether complex was added and stirred at 50° C. for 2 hours.

The reaction mixture was ice-cooled and then poured into 300 ml of water. The pH of the mixture was adjusted to about 2.5 with concentrated aqueous ammonia and the precipitates were collected by filtration and washed with water and then acetone, followed by drying, to obtain 9.98 g of the title compound (Yield: 70.9%).

$^1$H NMR (d$_6$-DMSO) δ:
2.51 (s, 3H), 3.40 (s, 2H), 4.52–4.77 (m, 2H), 5.02 (s, 2H), 8.22 (s, 1H).

SYNTHESIS EXAMPLE 7

Synthesis of 7-amino-3-[(5-carboxy-2-methyl-s-triazolo[1,5-a]pyrimidin-7-yl)thiomethyl]-3-cephem-4-carboxylic acid diphenylmethyl ester To a suspension of 9.9 g (23 mmole) of 7-amino-3-[(5-carboxy-2-methyl-s-triazolo[1,5-a]pyrimidin-7-yl)-thiomethyl-3-cephem-4-carboxylic acid, 70 ml of methanol and 200 ml of methylene chloride, diphenyl diazomethane synthesized from 19.63 g (100 mmole) of benzophenone hydrazone, 21.66 g (100 mmole) of mercuric oxide (yellow) and 150 ml of n-hexane and dissolved in 30 ml of methylene chloride was added dropwise over 2 hours and stirred at room temperature for 12 hours.

After filtration, the reaction mixture was concentrated and the residue obtained was crystallized with addition of isopropyl ether. The crystals obtained were collected by filtration and dried to obtain 11.57 g of the title compound (Yield: 66.6%).

$^1$H NMR (d$_6$-DMSO) δ:
2.65 (s, 3H), 3.58–3.82 (m, 2H), 4.23–4.48 (m, 2H), 4.83–5.17 (m, 2H), 7.02–8.05 (m, 23H).

EXAMPLE 37

Synthesis of
7-{2-[2-amino-1,3-thiazol-4-yl]-2-[1-(3-(3,4-dihydroxybenzoyl)carbazoyl-1-methylethoxyimino]acetamide}-3-[(5-carboxy-2-methyl-s-triazolo[1,5-a]pyrimidin-7-yl)-thiomethyl]-3-cephem-4-carboxylic acid.hydrochloride I. 5.52 g (12 mmole) of 2-(2-amino-1,3-thiazol-4-yl)-2-{1-[3-(3,4-dihydroxybenzoyl)carbazoyl]-1-methylethoxyimino}acetic acid.hydrochloride, 11.5 g (15.2 mmole) of 7-amino-3-[(5-carboxy-2-methyl-s-triazolo[1,5-a]pyrimidin-7-yl)thiomethyl]-3-cephem-4-carboxylic acid diphenylmethyl ester and 2.3 g (15 mmole) of 1-hydroxybenzotriazole were dissolved in 40 ml of DMF, followed by ice-cooling and 3.1 g (15 mmole) of DCC was added thereto. The mixture was stirred for 30 minutes under ice-cooling and further stirred at room temperature for 1 hour.

After filtration of the reaction mixture, the same amount of chloroform was added thereto and the mixture obtained was added dropwise into 4 liter of ether while vigorously stirring. The precipitates were collected by filtration, washed with ether and then dried to obtain 13.8 g of the desired diphenylmethyl ester (Yield: 96%).

II. To an ice-cooled mixture comprising 30 ml of trifluoroacetic acid and 10 ml of anisole, 3.26 g (2.7 mmole) of diphenylmethyl ester obtained above was added and stirred for 30 minutes. The mixture obtained was added dropwise into 1 liter of ether while vigorously stirring. The precipitates were collected by filtration, washed with ether and dried to obtain 1.46 g of the title compound (Yield: 62.5%).

$^1$H NMR (d$_6$-DMSO) δ:
1,60 (s, 6H), 2.62 (s, 3H), 3.81 (bs, 2H), 4.60 (bs, 2H), 5.34 (d, J=5Hz, 1H), 5.82-6.22 (m, 1H), 6.83-7.60 (m, 4H), 7.93 (s, 1H).

EXAMPLES 38 to 41

In the same manner as in Example 37, the following compounds were synthesized.

EXAMPLE 38

7-{2-[2-Amino-1,3-thiazol-4-yl]-2-[1-(3-(3,4-dihydroxybenzoyl)carbazoyl)-1-methylethoxyimino]acetamide}-3-[(s-triazolo[1,5-a]pyrimidin-7-yl)thiomethyl]-3-cephem-4-carboxylic acid.hydrochloride $^1$H NMR (d$_6$-DMSO) δ:
1.60 (s, 6H), 3.78 (s, 2H), 4.53 (m, 2H), 5.38 (d, J=4Hz, 1H), 5.86-6.17 (m, 1H), 6.78-7.66 (m, 5H), 8.22 (m, 2H).

EXAMPLE 39

7-{2-[2-Amino 1,3-thiazol-4-yl]-2-[1-(3-(3,4-dihydroxybenzoyl)carbazoyl)-1-methylethoxyimino}-3-[(5,6-dimethyl-s-triazolo[1,5-a]-pyrimidin-7-yl)thiomethyl]-3-cephem-4-carboxylic acid.hydrochloride $^1$H NMR (d$_6$-DMSO) δ:
1.62 (s, 6H), 2.51 (s, 3H), 2.63 (s, 3H), 3.73 (s, 2H), 4.43 (bs, 2H), 2.54 (d, J=4Hz, 1H), 5.76-6.11 (m, 1H), 6.81-7.62 (m, 4H), 8.72 (s, 1H).

EXAMPLE 40

7-{2-[2-Amino-1,3-thiazol-4-yl]-2-[1-(3-(3,4-dihydroxybenzoyl)carbazoyl)-1-methylethoxyimino]acetamide}-3-[(2-carboxy-s-triazolo[1,5-a]-pyrimidin-7-yl)thiomethyl]-3-cephem-4-carboxylic acid.hydrochloride

EXAMPLE 41

7-{2-[2-Amino-1,3-thiazol 4-yl]-2-[1-(3-(3,4-dihydroxybenzoyl)carbazoyl)-1-methylethoxyimino]acetamide}-3-[(2-carboxy-5,6-dimethyl-s-triazolo[1,5-a]pyrimidin-7-yl)-thiomethyl]-3-cephem-4-carboxylic acid.hydrochloride $^1$H NMR (d$_6$-DMSO) δ:
1.63 (s, 6H), 2.52 (s, 3H), 2.68 (s, 3H), 3.81 (s, 2H), 4.45 (bs, 2H), 5.28 (d, J=5Hz, 1H), 5.30-6.21 (m, 1H), 6.83-7.72 (m, 4H).

TEST EXAMPLE 3

Each of 20 mg/kg of the compounds obtained in Example 2, Example 25 and Example 28 was administered parenterally to Macaco and the half-time in blood was measured. The results are shown in Table 4.

The concentrations of the compounds were measured according to HPLC method. Novapack C18 or Microbondapack C18 (trade name, produced by Waters Co.) was used as a column. Further, cefpiramide was used as a control drug.

TABLE 4

| Compound | Half-time in blood of Macaco (hours) |
| --- | --- |
| Compound obtained in Example 2 (sodium salt) | 5.3 |
| Compound obtained in Example 25 (sodium salt) | 4.0 |
| Compound obtained in Example 28 (sodium salt) | 4.7 |
| Cefpiramide | 2.5 |

As is apparent from Table 4, the half-times in blood of the compounds according to the present invention are longer than that of cefpiramide in the case of Macaco. Among the existing cephalosporins, cefpiramide is known as a cephalosporin having a long prolonged time in blood. On the other hand, the fact that the half-times in blood of the β-lactam compounds in monkey and human being are mutually well-related has been reported by Y. Sawada et al. (J. Pharmaco., Biopharma., 12, 241 (1984). Accordingly, the results in Table 4 suggest that the half-times in blood of said compounds are longer than that of cefpiramide in the case of human beings. High usefulness such that the same or higher clinical effect is obtained with a smaller number of administration, when compared with other medicines, can be expected.

TEST EXAMPLE 4

The minimum inhibition concentrations (MIC) of the compounds obtained in the respective examples described above were measured according to the standard method of Japanese Chemotherapy Association. The results are shown in Table 5 and Table 6.

In Table 6, cephazoline (CAZ) was used as a control compound.

As is apparent from Table 5, the compounds of the present invention is effective to gram positive bacteria and gram negative bacteria and have wide range of antibacterial spectrum. Particularly, the compounds of the present invention exhibit strong antibacterial activities to glucose non-fermentable bacteria including Pseudomonas aeruginosa when compared with those of the third aged series cephalosporin.

As is apparent from Table 6, the compounds of the present invention exhibit strong antibacterial activities to a cephazoline resistance clinical separated strain which is one of the third aged series cephalosporins.

$^1$H NMR (d$_6$-DMSO) δ:
1.58 (s, 6H), 2.67 (s, 3H), 3.44 (s, 2H), 4.35 (bs, 2H), 5.49 (d, J=5Hz, 1H), 5.94–6.42 (m, 1H), 6.98–7.90 (m, 22H), 8.25 (s, 1H), 8.73 (s, 1H), 8.96 (s, 1H).

EXAMPLE 42

Synthesis of 7-[2-(2-amino-1,3-thiazol-4-yl)-2-(1-carbazoyl-1-

TABLE 5

| Strain | Example | MIC (μg/ml) | | | | | | | | | | | |
|---|---|---|---|---|---|---|---|---|---|---|---|---|---|
| | | 12 | 38 | 37 | 29 | 36 | 33 | 39 | 41 | 25 | 27 | 28 | CAZ |
| S. aureus | Smith | 3.13 | 1.56 | 25 | 1.56 | 6.25 | 25 | 12.5 | 25 | 6.25 | 25 | 12.5 | 6.25 |
| | IAA498 | 6.25 | 3.13 | 25 | 3.13 | 12.5 | 25 | 12.5 | 50 | 12.5 | 50 | 25 | 12.50 |
| E. coli | ML4707 | <0.006 | 0.012 | 0.012 | <0.006 | 0.012 | <0.006 | <0.006 | <0.006 | <0.006 | 0.012 | 0.012 | 0.05 |
| | GN5482 | 0.012 | 0.025 | 0.012 | 0.025 | 0.012 | <0.006 | <0.006 | <0.006 | <0.006 | <0.006 | <0.006 | 0.78 |
| K. pneumoniae | 4at521 | 0.012 | 0.012 | <0.006 | 0.012 | 0.012 | <0.006 | 0.012 | <0.006 | <0.006 | <0.006 | <0.006 | 0.10 |
| E. colacae | GN7471 | 1.56 | 3.13 | 0.78 | 1.56 | 3.13 | 0.39 | 1.56 | 0.39 | 3.13 | 0.78 | 0.78 | 3.13 |
| | 908RN | 3.13 | 25 | 0.78 | 6.25 | 3.13 | 0.2 | 1.56 | 0.2 | 1.56 | 0.39 | 0.78 | 100.00 |
| C. freundii | GN7391 | 6.25 | 25 | 1.56 | 6.25 | 3.13 | 0.39 | 3.13 | 0.39 | 6.25 | 0.78 | 0.78 | >100.00 |
| S. marcescens | GN10857 | 0.39 | 0.39 | 0.2 | 0.39 | 0.39 | 0.05 | 0.2 | 0.1 | 0.1 | 0.1 | 0.2 | 1.56 |
| P. vulgaris | Gn7919 | 0.78 | 1.56 | 0.78 | 6.25 | 0.78 | 0.2 | 0.78 | 0.39 | 0.39 | 0.39 | 0.78 | 1.56 |
| P. aeruginosa | GN10362 | 0.1 | 0.1 | 0.05 | 0.39 | 0.2 | 0.05 | 0.2 | 0.1 | 0.025 | 0.05 | 0.05 | 1.56 |
| | 4au542 | 0.2 | 0.1 | 0.2 | 0.78 | 0.39 | 0.2 | 0.39 | 0.2 | 0.1 | 0.2 | 0.39 | 1.56 |
| | 5D58-1 | 0.2 | 0.39 | 0.78 | 0.39 | 0.78 | 0.2 | 0.78 | 0.39 | 0.05 | 0.2 | 0.1 | 0.78 |
| P. cepacia | OF189 | 0.012 | 0.025 | <0.006 | <0.006 | 0.012 | <0.006 | <0.006 | <0.006 | <0.006 | 0.012 | 0.012 | 3.13 |
| P. maltophilia | OF247 | 0.39 | 0.78 | 0.39 | 0.2 | 0.2 | 0.1 | 0.2 | 0.1 | 0.1 | 0.2 | 0.39 | 3.13 |

TABLE 6

| Strain | Example | MIC (μg/ml) | | | | | | | | | | |
|---|---|---|---|---|---|---|---|---|---|---|---|---|
| | | 12 | 37 | 29 | 36 | 33 | 39 | 41 | 25 | 27 | 28 | CAZ |
| E. cloacae | 5D52-2 | 0.2 | 0.1 | 0.78 | 0.2 | 0.1 | 0.39 | 0.05 | 0.39 | 0.1 | 0.1 | 12.5 |
| | 5D63-2 | 3.13 | 0.2 | 0.78 | 0.39 | 0.1 | 0.2 | 0.1 | 0.39 | 0.2 | 0.2 | 12.5 |
| | 1V25 | 12.5 | 6.25 | 3.13 | 12.5 | 1.56 | 12.5 | 1.56 | 6.25 | 0.39 | 0.2 | 50 |
| | 1Y247 | 25 | 3.13 | 0.78 | 12.5 | 1.56 | 1.56 | 0.39 | 12.5 | 0.78 | 0.78 | 12.5 |
| | 908RN | 3.13 | 0.78 | 3.13 | 12.5 | 0.2 | 3.13 | 0.2 | 3.13 | 0.78 | 1.56 | >100 |
| C. freundii | 5D60-1 | 3.13 | 0.39 | 0.39 | 1.56 | 0.2 | 0.39 | 0.1 | 0.78 | 6.25 | 12.5 | >100 |
| | 1R523 | 0.78 | 0.1 | 0.2 | 0.2 | 0.05 | 0.1 | 0.025 | 0.2 | 0.2 | 0.2 | 25 |
| | 1R524 | 0.78 | 0.1 | 0.78 | 0.2 | 0.025 | 0.1 | 0.006 | 0.1 | 0.1 | 0.1 | 25 |
| | 1R526 | 1.56 | 0.1 | 0.2 | 0.2 | 0.025 | 0.1 | 0.025 | 0.2 | 0.1 | 0.1 | 25 |
| | 1R527 | 0.78 | 0.1 | 0.78 | 0.2 | 0.025 | 0.1 | 0.012 | 0.1 | 0.1 | 0.1 | 25 |
| | 1U589 | 1.56 | 0.2 | 0.78 | 0.39 | 0.05 | 0.39 | 0.05 | 0.39 | 0.39 | 0.39 | 100 |
| | 1U692 | 3.13 | 0.2 | 12.5 | 0.39 | 0.05 | 0.39 | 0.05 | 0.39 | 0.2 | 0.39 | 100 |
| | GN7391 | 25 | 3.13 | 0.012 | 6.25 | 0.78 | 3.13 | 0.39 | 6.25 | 0.78 | 1.56 | >100 |

SYNTHESIS EXAMPLE 8

Synthesis of 7-{2-(2-formylamino-1,3-thiazol-4-yl)-2-[1-(3-formylcarbazoyl)-1-methylethoxyimino]acetamide)-3-[(3-carboxy-5-methylpyrazolo[1,5-a]pyrimidin-7-yl)thiomethyl]-3-cephem-4-carboxylic acid diphemylmethyl ester 1.72 g (5 mmole) of 2-(2-formylamino-1,3-thiazol-4-yl)-2-[1-(3-formylcarbazoyl)-1-methylethoxyimino]acetic acid, 4.15 g (5.5 mmole) of 7-amino-3-[(3-carboxy-5-methylpyrazolo[1,5-a]pyrimidin-7-yl)thiomethyl]-3-cephem-4-carboxylic acid diphenylmethyl ester and 0.92 g (6 mmole) of 1-hydroxybenzotriazole were dissolved in 20 ml of DMF, followed by ice-cooling and 1.24 g (6 mmole) of DCC was added thereto. The mixture was stirred for 30 minutes under ice-cooling and further stirred at room temperature for 1 hour. After filtration of the reaction mixture, the same amount of chloroform was added thereto and the mixture obtained was added dropwise into 1 liter of ether while vigorously stirring. The precipitates were collected by filtration, washed with ether and then dried. The crude crystals obtained were purified through a silica gel chromatography (eluting solution: chloroform-2% methanol-chloroform) to obtain 3.3 g of the title compound (Yield: 61%).

methylethoxyimino)acetamide]-3-[(3-carboxy-5-methylpyrazolo[1,5-a]pyrimidin-7-yl)thiomethyl]-3-cephem-4-carboxylic acid diphenylmethyl ester.dihydrochloride To 40 of methanol ice-cooled, 1.38 g (9 mmole) of phosphorus oxychloride and then 3.25 g (3 mmole) of 7-{2-(2-formylamino-1,3-thiazol-4-yl)-2-[1-(3-formylcarbazoyl)-1-methylethoxyimino]acetamide}-3-[(3-carboxy-5-methylpyrazolo[1,5-a]pyrimidin-7-yl)thiomethyl]-3-cephem-4-carboxylic acid diphenylmethyl ester were added. The mixture obtained was stirred for 1 hour under ice-cooling and added dropwise into 500 ml of ether while vigorously stirring. The precipitates were collected by filtration and then dried to obtain 3.28 g of the title compound (Yield: 99%).

$^1$H NMR (d$_6$-DMSO) δ:
1.60 (s, 6H), 2.65 (s, 3H), 3.44 (s, 2H), 4.37 (bs, 2H), 5.50 (d, J=5Hz, 1H), 5.92–6.38 (m, 1H), 6.96–7.96 (m, 22H), 8.98 (s, 1H).

EXAMPLE 43

Synthesis of
7-[2-(2-amino-1,3-thiazol-4-yl)-2-(1-carbazoyl-1-methylethoxyimino)acetamide]-3-[(carboxy-5-methylpyrazolo[1,5-a]pyrimidin-7-yl)thiomethyl]-3-cephem-4-carboxylic acid.dihydrochloride To an ice-cooled mixture comprising 25 ml of trifluoroacetic acid and 7 ml of anisole, 3.28 g (3 mmole) of 7-[2-(2-amino-1,3-thiazol-4-yl)-2-(1-carbazoyl-1-methylethoxyimino)acetamide]-3-[(3-carboxy-5-methyl-pyrazolo[1,5-a]pyrimidin-7-yl)thiomethyl]-3-cephem-4-carboxylic acid diphenylmethyl ester dihydrochloride was added and stirred for 30 minutes. The mixture obtained was added dropwise into 500 ml of ether while vigorously stirring. The precipitates were collected by filtration, washed with ether and then dried to obtain 2.25 g of the title compound (Yield: 98%).

$^1$H NMR (d$_6$-DMSO) δ:
1.58 (s, 6H), 2.63 (s, 3H), 3.77 (s, 2H), 4.45 (bs, 2H), 5.32 (d, J=5Hz, 1H), 5.75–6.12 (m, 1H), 6.96–7.48 (m, 2H), 8.58 (s, 1H).

EXAMPLE 44

Synthesis of
7-{2-[2-amino-1,3-thiazol-4-yl]-2-[1-(3-(3,4-diacetozybenzoyl)carbazoyl)-1-methylethoxyimino]acetamide}-3-[(3-carboxy-5-methyl-pyrazolo[1,5-a]pyrimidin-7-yl)thiomethyl-3-cephem-4-carboxylic acid To a solution of 2.4 g (3.14 mmole) of 7-[2-(2-amino-1,3-thiazol-4-yl)-2-(1-carbazoyl-1-methylethoxyimino)acetamide]-3-[(3-carboxy-5-methyl-pyrazolo[1,5-a]pyrimidin-7-yl)thiomethyl]-3-cephem-4-carboxylic acid.dihydrochloride suspended in 30 ml of methylene chloride, 6.39 g (31.4 mmole) of N,O-bis(-trimethylsilyl)acetamide was added and stirred for 30 minutes. After the solution obtained was ice-cooled, while stirring, 0.9 g (3.5 mmole) of 3,4-diacetoxybenzoic acid chloride was added thereto and stirred for 1 hour. The reaction mixture was poured into 500 ml of ether and a small amount of methanol was added thereto while stirring. The precipitates were collected by filtration, washed with ether and then dried. The crystals obtained were dissolved in a solution containing water and 5% sodium bicarbonate and, while stirring, the pH thereof was adjusted to 2 with a 2N hydrochloric acid. The crystals precipitated were collected by filtration, washed with water and then dried to obtain 2.52 g of the title compound (Yield: 88%).

$^1$H NMR (d$_6$-DMSO) δ:
1.57 (s, 6H), 2.33 (s, 6H), 2.62 (s, 3H), 3.83 (bs, 2H), 4.50 (bs, 2H), 5.40 (d, J=5Hz, 1H), 5.92–6.23 (m, 1H), 7.10 –8.18 (m, 5H), 8.70 (s, 1H).

EXAMPLES 45 to 55

In the same manner as in Example 44, the following compounds were prepared.

EXAMPLE 45

7-{2-[2-Amino-1,3-thiazol-4-yl]-2-[1-(3-(3,4-diacetoxybenzoyl)carbazoyl)-1-methylethoxyimino]acetamido}-3-[(2-carboxy-5-methyl-s-triazolo[1,5-a]pyrimidin-7-yl)thiomethyl]-3-cephem-4-carboxylic acid $^1$H NMR (d$_6$-DMSO) δ:
1.64 (s, 6H), 2.37 (s, 6H), 2.69 (s, 3H), 3.85 (s, 2H), 4.60 (bs, 2H), 5.44 (d, J=5Hz, 1H), 5.85–6.24 (m, 1H), 6.84–7.71 (m, 5H).

EXAMPLE 46

7-{2-[2-Amino-1,3-thiazol-4-yl]-2-[1-(3-(3,4-diacetoxybenzoyl)carbazoyl)-1-methylethoxyimino]acetamido}-3-[(2-carboxy-s-triazolo[1,5-a]pyrimidin-7-yl)thiomethyl]-3-cephem-4-carboxylic acid $^1$H NMR (d$_6$-DMSO) δ:
1.60 (s, 6H), 2.35 (s, 6H), 3.82 (s, 2H), 4.57 (bs, 2H), 5.39 (d, J=5Hz, 1H), 5.86–6.23 (m, 1H), 6.80–7.74 (m,5H), 8.92 (d, J=4Hz, 1H).

EXAMPLE 47

7-{2-[2-Amino-1,3-thiazol-4-yl]-2-[1-(3-(3,4-diacetoxybenzoyl)carbazoyl)-1-methylethoxyimino]acetamido}-3-[(3-carboxy-5,6-dimethylpyrazolo[1,5-a]pyrimidin-7-yl)thiomethyl]-3-cephem-4-carboxylic acid $^1$H NMR (d$_6$-DMSO) δ:
1.62 (s, 6H), 2.34 (s, 6H), 2.51 (s, 3H), 2.64 (s, 3H), 3.82 (s, 2H), 4.50 (bs, 2H), 5.21 (d, J=5Hz, 1H), 5.74–6.18 (m, 1H), 6.81–7.65 (m, 4H), 8.66 (s, 1H).

EXAMPLE 48

7-{2-[2-Amino-1,3-thiazol-4-yl]-2-[1-(3-(3,4-diacetoxybenzoyl)carbazoyl)-1-methylethoxyimino]acetamido}-3-[(5-methyl-2-trifluoromethyl-s-triazolo[1,5-a]pyrimidin-7-yl)-thiomethyl]-3-cephem-4-carboxylic acid $^1$H NMR (d$_6$-DMSO) δ:
1.64 (s, 6H), 2.36 (s, 6H), 2.70 (s, 3H), 3.83 (s, 2H), 4.58 (bs, 2H), 5.40 (d, J=5Hz, 1H), 5.86–6.20 (m, 1H), 6.82–7.77 (m, 5H).

EXAMPLE 49

7-{2-[2-Amino-1,3-thiazol-4-yl[-2-[1-(3-(3,4-diacetoxybenzoyl)carbazoyl)-1-methylethoxyimino]acetamido}-3-[(2-carboxy-6,7-dihydro-5H-cyclopenta[f]-s-triazolo[1,5-a]pyrimidine-8-yl)thiomethyl]-3-cephem-4-carboxylic acid $^1$H NMR (d$_6$-DMSO) δ:
1.63 (s, 6H), 1.98–2.45 (m, 8H), 2.88–3.42 (m, 4H), 3.84 (s, 2H), 4.48 (bs, 2H), 5.28 (d, J=5Hz, 1H), 5.81–6.16 (m, 1H), 6.88–7.67 (m, 4H).

EXAMPLE 50

7-{2-[2-Amino-1,3-thiazol-4-yl]-2-[1-(3-(3,4-diacetoxybenzoyl)carbazoyl)-1-methylethoxyimino]acetamido}-3-[(3-carboxy-6,7-dihydro-5H-cyclopenta[f-]pyrazolo[1,5-a]pyrimidine-8-yl)thiomethyl]-3-cephem-4-carboxylic acid $^1$H NMR (d$_6$-DMSO) δ:
1.62 (s, 6H), 2.0–2.46 (m, 8H), 2,81–3.40 (m, 4H), 3.85 (s, 2H), 4.50 (bs, 2H), 5.25 (d, J=5Hz, 1H), 5.83–6.15 (m, 1H), 6.89–7.66 (m, 4H), 8.68 (s, 1H).

EXAMPLE 51

7-{2-[2-Amino-1,3-thiazol-4-yl]-2-[1-(3-(3,4-diacetoxybenzoyl)carbazoyl)-1-methylethoxyimin]acetamido}-3-[(2,5-dimethylpyrazolo[1,5-a]pyrimidine-8-yl)thiomethyl]-3-cephem-4-carboxylic acid $^1$H NMR (d$_6$-DMSO) δ:
1.63 (s, 6H), 2.33 (s, 6H), 2.48 (s, 3H), 2.60 (s, 3H), 3.84 (s, 2H), 4.48 (bs, 2H), 5.44 (d, J=5Hz, 1H), 5.86–6.20 (m, 1H), 6.45 (s, 1H), 6.88–7.43 (m, 5H).

EXAMPLE 52

7-{2-[2-Amino-1,3-thiazol-4-yl]-2-[1-(3-(3,4-diacetoxybenzoyl)carbazoyl)-1-methylethoxyimino]acetamido}-3-[(5-methylpyrazolo[1,5-a]pyrimidine-8-yl)thiomethyl]-3-cephem-4-carboxylic acid $^1$H NMR (d$_6$-DMSO) δ:
1.58 (s, 6H), 2.37 (s, 6H), 2.61 (s, 3H), 3.84 (s, 2H), 4.54 (bs, 2H), 5.44 (d, J=5Hz, 1H), 5.88–6.20 (m, 1H), 6.74 (d, J=2Hz, 1H), 6.96–7.66 (m, 5H), 8.37 (d, J=2Hz, 1H).

EXAMPLE 53

Synthesis of
7-{2-[2-amino-1,3-thiazol-4-yl]-2-[1-(3-(3,4-diacetoxybenzoyl)carbazoyl)-1-methylethoxyimino]acetamido}-3-[(3-carboxy-5-methylpyrazolo[1,5-a]pyrimidin-7-yl)thiomethyl-3-cephem-4-carboxylic acid sodium salt A suspension obtained by adding 200 ml of water to 2.5 g (2.7 mmole) of 7-{2-[2-amino-1,3-thiazol-4-yl]-2-[1-(3-(3,4-diacetoxybenzoyl)carbazoyl)-1-methylethoxyimino[acetamide}-3-[(3-carboxy-5-methylpyrazolo[1,5-a]pyrimidin-7-yl)thiomethyl-3-cephem-4-carboxylic acid, was dissolved at pH 6 by adding 5% sodium bicarbonate aqueous solution. The mixture obtained was adsorbed to a column charged with 100 ml of HP-20 and filled up with water, and then washed with water. The title compound was eluted by 50% methanol-water and after evaporation of methanol, lyophilized to obtain 1.69 g of the title compound (Yield: 67%).

$^1$H NMR (d$_6$-DMSO) δ:
1.62 (s, 6H), 2.36 (s, 6H), 2.66 (s, 3H), 3.84 (s, 2H), 4.50 (bs, 2H), 5.42 (d, J=5Hz, 1H), 5.88–6.23 (m, 1H), 6.98–7.99 (m, 5H), 8.68 (s, 1H).

EXAMPLES 54 to 58

In the same manner as in Example 25, the compounds of Examples 54, 57 and 58, and in the same manner as in Example 37, the compounds of Examples 55 and 56 were prepared, respectively.

EXAMPLE 54

7-{2-[2-Amino-1,3-thiazol-4-yl]-2-[1-(3-(3,4-dihydroxybenzoyl)carbazoyl)-1-methylethoxyimino]acetamido}-3-[(3-carboxypyrazolo[1,5-a]pyrimidin-7-yl)thiomethyl]-3-cephem-4-carboxylic acid $^1$H NMR (d$_6$-DMSO) δ:
1.58 (s, 6H), 3.78 (s, 2H), 4.62 (bs, 2H), 5.44 (d, J=5Hz, 1H), 5.85–6.18 (m, 1H), 6.85–7.63 (m, 6H), 8.72 (s, 1H).

EXAMPLE 55

7-{2-[2-Amino-1,3-thiazol-4-yl]-2-[1-(3-(3,4-dihydroxybenzoyl)carbazoyl)-1-methylethoxyimino]acetamido}-3-[(5-methyl-2-trifluoromethyl-s-triazolo[1,5-a]pyrimidin-7-yl)-thiomethyl]-3-cephem-4-carboxylic acid $^1$H NMR (d$_6$-DMSO) δ:
1.63 (s, 6H), 2,72 (s, 3H), 3.82 (s, 2H), 4.58 (bs, 2H), 5.40 (d, J=5Hz, 1H), 5.90–6.22 (m, 1H), 6.84–7.78 (m, 5H).

EXAMPLE 56

7-{2-[2-Amino-1,3-thiazol-4-yl]-2-[1-(3-(3,4-dihydroxybenzoyl)carbazoyl)-1-methylethoxyimino]acetamido}-3-[(2-carboxy-s-triazolo[1,5-a]pyrimidin-7-yl)thiomethyl]-3-cephem-4-carboxylic acid $^1$H NMR (d$_6$-DMSO) δ:
1.58 (s, 6H), 3.82 (bs, 2H), 4.53 (bs, 2H), 5.38 (d, J=5Hz, 1H), 5.88–6.22 (m, 1H), 6.78–7.76 (m, 5H), 8.93 (d, J=4Hz, 1H).

EXAMPLE 57

7-{2-[2-Amino-1,3-thiazol-4-yl]-2-[1-(3-(3,4-dihydroxybenzoyl)carbazoyl)-1-methylethoxyimino]acetamido}-3-[(2,5-dimethylpyrazolo[1,5-a]pyrimidin-7yl)thiomethyl]-3-cephem-4-carboxylic acid $^1$H NMR (d$_6$-DMSO) δ:
1.64 (s, 6H), 2.47 (s, 3H), 2.58 (s, 3H), 3.86 (s, 2H), 4.48 (bs, 2H), 5.47 (d, J=5Hz, 1H), 5.88–6.18 (m, 1H), 6.48 (s, 1H), 6.87–7.58 (m, 5H).

EXAMPLE 58

7-{2-[2-Amino-1,3-thiazol-4-yl]-2-[1-(3-(3,4-dihydroxybenzoyl)carbazoyl)-1-methylethoxyimino]acetamido}-3-[(5-methylpyrazolo[1,5-a]pyrimidin-7-yl)thiomethyl]-3-cephem-4-carboxylic acid $^1$H NMR (d$_6$-DMSO) δ:
1.52 (s, 6H), 2.60 (s, 3H), 3.84 (s, 2H), 4.52 (bs, 2H), 5.42 (d, J=5Hz, 1H), 5.92–6.24 (m, 1H), 6.74 (d, J=2Hz, 1H), 6.94–7.64 (m, 5H), 8.37 (d, J=2Hz, 1H).

EXAMPLE 59

Synthesis of
7-{2-[2-amino-1,3-thiazol-4-yl]-2-[1-(3-(3,4-dihydroxybenzoyl)carbazoyl)-1-methylethoxyimino]acetamido}-3-[(2-carboxy-5-methyl-s-triazolo[1,5-a]pyrimidin-7-yl)-thiomethyl]-3-cephem-4-carboxylic acid 5.76 g of 7-(2-amino-1,3-thiazol-4-yl-glyoxylamide)-3-[(2-carboxy-5-methyl-s-triazolo[1,5-a]pyrimidin-7-yl)thiomethyl]-3-cephem-4-carboxylic acid and 4.57 g of 1-(2-aminooxy-2-methylpropionyl)-2-(3,4-dihydroxybenzoyl)hydrazinehydrochloride were dissolved in 80 ml of dimethylacetamide. After 24 hours the solution was concentrated under reduced pressure. 250 ml of water were then added with stirring. The precipitated material is collected, washed successively with water, acetone and ether and dired in vacuo at 40° C. The product is 7-{2-[2-amino-1,3-thiazol-4-yl]-2-[1-(3-(3,4-dihyroxybenzoyl)carbozoyl)-1-methylethoxy]imino]acetamido}-3-[(2-carboxy-5-methyl-s-triazolo[1,5-a]pyrimidin-7-yl]thiomethyl]-3-cephem-4-carboxylic acid.

This produce (2.07 g) was dissolved in 20 ml of dimethylformamide and 20 ml of ethanol. A 2N solution of sodium-2-ethylcaproate in acetone (3 ml) was added. The precipitated disodium salt was collected, washed with ethanol and n-hexane and dried in vacuo at 30° C.

| Analysis: | C | H | N | S |
|---|---|---|---|---|
| Calc. | 42.71 | 3.12 | 17.67 | 11.03% |
| Found | 43.55 | 3.24 | 18.08 | 10.71% |

1-(2-Aminooxy-2-methylpropionyl)-2-(3,4-dihydroxybenzoyl)-hydrazine.hydrochloride can be prepared as follows:

1. 2-Methyl-2-(phthalimidooxy)propionic acid-allyl ester

To a solution of 58 g of allyl alcohol and 316 g of pyridine in 1 liter of methylene chloride was added dropwise 230 g of α-bromo-isobutyric acid bromide under ice-cooling. After 1.5 hours, the mixture obtained was added to 1 liter of 3 N hydrochloric acid and the organic phase was separated and washed successively with each 1 liter of 0.5 N hydrochloric acid, 0.5 M aqueous sodium bicarbonate and water. Then the solvent was evaporated. The residue was added to a suspension of 146.8 g of N-hydroxyphthalimide, 165.8 g of potassium carbonate and 20 g of potassium iodide in 1 liter of DMSO. The mixture was stirred for 4 hours at 60° C. After cooling, the mixture was poured into 6 liters of water and the product was extracted with 3 liters of ethyl acetate. After washing twice with 0.5 liter of a sodium chloride solution, the solvent was evaporated and the residue was recrystallized from 0.6 liter of tert-butyl methyl ether and 1.5 liters of hexane to obtain the product, m.p. 51°-53° C.

2. 2-Methyl-2(phthalimidooxy)propionic acid

The allyl ester (187.6 g) which was obtained in Step 1 was dissolved in 1.5 liters of acetonitrile. After addition of 1 g of palladium-(II)-acetate, 6.5 ml of triethylphosphite and 62.4 g of N-methylpyrrolidine, the mixture was stirred for 2 hours at room temperature. The solvent was evaporated, and the residue was partitioned between 0.5 liter of water and 0.5 liter of ethyl acetate. The aqueous phase was then adjusted to pH 3-4 with 150 ml of 3N aqueous HCl. After cooling, the product was filtered. m.p. 133°-135° C.

3. 2-Methyl-2-(phthalimidooxy)propionic acid-2-benzothiazolylthiol ester 148.2 g of triphenylphosphine and 187.9 of bis-(benzothiazol-2-yl)disulfide in 2 liters of methylene chloride were stirred for 2 hours at room temperature. After cooling to 0°-5° C., 98 g of the acid which was obtained in Step 2 was added thereto and stirred at 0°-5° C. for further 3 hours. Undissolved material was filtered off and the filtrate was evaporated. The residue was crystallized from 1 liter of ethyl acetate. After filtration, the crystal was again suspended in 1 liter of isopropanol, filtered by suction and dried. The product obtained has a melting point of 170°-172° C.

4. 3,4-Dihydroxybenzoic acid methyl ester

A mixture of 180 g of 3,4-dihydroxybenzoic acid, 360 ml of dichloroethane, 142 ml of methanol and 18 g of p-toluenesulfonic acid was boiled on a water separator, until distillate is clear. The solvent was evaporated, and the residue was admixed with 1.5 liters of diethyl ether, washed with 1 liter of a saturated aqueous sodium bicarbonate solution and twice with each 0.4 liter of aqueous sodium chloride solution. After evaporation again, the residue was recrystallized from 3 liters of toluene to obtain the product. m.p. 136°-137° C.

5. 3,4-Dihydroxybenzohydrazide 120 g of 3,4-dihydroxybenzoic acid methyl ester was subjected to reaction with 340 ml of methanol and 340 ml of hydrazine hydrate over 3 days at room temperature. Then 340 ml of water was added thereto and the solvent was evaporated in vacuum. Addition of water and evaporation were repeated twice. Subsequently the product was crystallized from 340 ml of water. m.p. 260° C. (decomposed).

$C_7H_8N_2O_3$: C: 49.70%, calc. 50.00%,
H: 4.87%, calc. 4.80%,
N: 16.40%, calc. 16.66%.

6. 1-(3,4-Dihydroxybenzoyl)-2-[2-methyl-(2-phthalimidooxy)propionyl]hydrazine

To 23.2 g of 3,4-dihydroxybenzohydrazide in 1 liter of methylene chloride was added 56.1 g of bis-trimethylsilyl-acetamide and the mixture was boiled for 2 hours under reflux. After cooling to room temperature, 55 g of 2-methyl-2-(phthalimidooxy)propionic acid-2-benzothiazolethiol ester was added thereto and stirred for 24 hours at room temperature. After evaporation of the solvent, the residue was boiled in 0.5 liter of ethanol for several minutes and evaporated in vacuum. Recrystallization from 0.5 liter of ethanol gives the product. m.p. 233°-235° C.

$C_{19}H_{17}N_3O_7$: C: 57.11%, calc. 57.14%,
H: 4.41%, calc. 4.29%,
N: 10.49%, calc. 10.52%.

7. 1-[2-(Aminooxy)-2-methylpropionyl]-2-(3,4-dihydroxybenzoyl)hydrazine hydrochloride To a suspension of 46.7 g of 1-(3,4-dihydroxybenzoyl)-2-[2-methyl-(2-phthalimidooxy)propionyl]hydrazine in 400 ml of ethanol was added 5.85 g of hydrazine hydrate and the mixture was stirred for 1 hour at room temperature. After filtrating undissolved substances off, the solvent was evaporated, and the residue was admixed again in 120 ml of ethanol, filtered and mixed with 23.4 ml of 5 N ethanolic hydrochloric acid and then mixed dropwise with 0.5 liter of diethyl ether. The crystal was recrystallized from 140 ml of ethanol for purification to obtain the product. m.p. 198°-201° C. (decomposed).

$C_{11}H_{15}N_3O_5 \cdot HCl \cdot C_2H_5OH$
C: 43.91%, calc. 44.39%,
H: 6.28%, calc. 6.30%,
N: 12.04%, calc. 11.95%,
Cl: 10.01%, calc. 10.08%.

7-(2-Amino-1,3-thiazol-4-yl-glyoxylamide)-3-[(2-carboxy-5-methyl-s-triazolo[1,5-a]pyrimidin-7-yl)thiomethyl]-3-cephem-4-carboxylic acid was synthesized as follows:

20 g of 7-aminocephalosporanic acid and 20 g of 7-mercapto-5-methyl-s-triazolo[1,5-a]pyrimidine-2-carboxylic acid were suspended in 240 ml of acetonitrile, and 120 ml of a 20% solution a boron trifluoride in acetonitrile were added thereto. The resulting solution is kept for 12 hours at room temperature, and 600 ml of water were then added thereto. The pH was adjusted to 2 by means of aqueous ammonia. The precipitated material was collected, washed successively with water, tetrahydrofuran and ether and dired in vacuo of 40° C. One obtained 7-amino-3-carboxy-5-methyl-s-triazolo[1,5-a]pyrimidin-7-yl)thiomethyl]-3-cephem-4-carboxylic acid.

| Analysis: | C | H | N | S |
|---|---|---|---|---|
| Calc. | 42.65 | 3.34 | 19.89 | 15.18% |
| Found | 41.94 | 3.67 | 20.64 | 15.10% |

29.5 g of 7-amino-3-[(2-carboxy-5-methyl-s-triazolo[1,5-a]pyrimidin-7-yl)thiomethyl-3-cephem-4-carboxylic acid were suspended in 700 ml of methylene chloride. Upon addition of 50.4 ml of N,O-bis-(trimethylsilyl)acetamide, the reaction mixture is stirred for 90 min. The solution is cooled to 5° C., 31.5 g of 5-(2-benzothiazolyl)-2-aminothio-4-thiazole glyoxylate were added and the reaction mixture was stirred for 2 hours at room temperature. The solution was concentrated to a volume of about 100 ml. 500 ml of methanol are then added. The precipitated material was collected and dried in vacuo of 40° C. One obtained 7-(2-amino-1,3-thiazol-4-yl-glyoxylamide)-3-[(2-carboxy-5-methyl-s-triazolo[1,5-a]pyrimidin-7-yl)thiomethyl]-3-cephem-4-carboxylic acid.

| Analysis: | C | H | N | S |
|---|---|---|---|---|
| Calc. | 41.66 | 2.8 | 19.43 | 16.68% |
| Found | 41.87 | 2.87 | 19.24 | 16.51% |

EXAMPLE 60

Synthesis of
7-{2-[2-amino-1,3-thiazol-4-yl]-2-[1-(3-(2,3-dihydroxybenzoyl)carbazoyl)-1-methylethoxyimino]acetamido}-3-[(2-carboxy-5-methyl-s-triazolo[1,5-a]pyrimidin-7-yl)-thiomethyl]-3-cephem-4-carboxylic acid 0.69 g of 1-(2-aminooxy-2-methylpropionyl)-2-(2,3-dihydroxybenzoyl)hydrazine-hydrochloride were added to a solution of 1.0 g of
7-(2-amino-1,3-thiazol-4-yl-glyoxylamido)-3-[(2-carboxy-5-methyl-s-triazolo[1,5-a]pyrimidin-7-yl)thiomethyl]-3-cephem-4-carboxylic acid in 15 ml of N,N-dimethylacetamide. After 24 hours the solvent was evaporated in vacuo at 30° C. Upon addition of 15 ml of water the crude product was precipitated. This was redissolved in 10 ml of methanol and 0.5 ml of triethylamine. Addition of 1.75 ml of a 1N aqueous solution of sodium 2-ethylcaproate in ethyl acetate precipitates the sodium salt, which was again dissolved in 10 ml of water. By addition of 2.3 ml of aqueous 1N HCl the product was obtained as a colorless solid, which was washed in ethanol and ether and dried. The product was
7-{2-[2-amino-1,3-thiazol-4-yl]-2-[1(3-(2,3-dihydroxy benzoly)carbazoyl]-1-methylethoxyimino]acetamido}-3-[(2-carboxy-5-methyl-s-triazolo[1,5-a]pyrimidin-7-yl)thiomethyl]-3-cephem-4-carboxylic acid.

$^1$H NMR (d$_6$-DMSO) δ:
1.49 (s, 3H), 1.52 (s, 3H), 2.61 (s, 3H), 3.64 (d, 1H), 3.82 (d, 1H), 4.37 (d, 1H), 4.56 (d, 1H), 5.22 (d, 1H), 5.88 (dd, 1H), 6.87 (s, 1H), 7.42 (s, 1H), 6.76 (m, 1H), 6.96 (m, 1H), 7.37 (s, 1H), 9.63 (d, 1H).

The 1-(2-aminooxy-2-methylpropionyl)-2-(2,3-dihydroxybenzoyl)hydrazine.hydrochloride can be prepared from 2,3-dihydroxybenzoic acid in analogy to Example 59. Melting point: 208°–211° C. (decomposed).

EXAMPLES 61-63

In a manner analogous to Example 59, there were obtained the following compounds.

EXAMPLE 61

7-{2-[2-Amino-1,3-thiazol-4-yl]-2-[1-(3-(3,4-dihydrdoxybenzoyl)carbazoyl]-1-methylethoxyimino]acetamido}-3-[(2-cyano-5-methyl-s-triazolo[1,5-a]pyrimidin-7-yl)thiomethyl]-3-cephem-4-carboxylic acid MS: 809 (M+H$^+$)
IR: (KBr) 1770 cm$^{-1}$
$^1$H NMR (d$_6$-DMSO) δ:
1.46 (s, 3H), 1.51 (s, 3H), 2.61 (s, 3H), 3.42 (d, 1H, J=17.5Hz), 3.76 (d, 1H, J=17.5Hz), 4.41 (d, 1H, J=12.5Hz), 4.62 (d, 1H, J=12.5Hz), 5.10 (d, 1H, J=5Hz), 5.76 (dd, 1H, J=5Hz, J=8Hz), 6.76 (d, 1H, J=7.5Hz), 7.22 (dd, 1H, J=7.5Hz, J=2.5Hz), 7.29 (d, 1H, J=2.5Hz, this is superimposed on a (s, 2H)), 7.91 (s, 1H), 9.24 (s, H, broad), 9.56 (d, 1H, J=8Hz), 9.60 (d, 1H, J=8Hz), 9.60 (s, 1H, broad), 9.90 (s, 1H, broad), 10.0 (s, 1H, broad).

EXAMPLE 62

7-{2-[2-Amino-1,3-thiazol-4-yl]-2-[1-(3-(3,4-dihydroxybenzoyl)carbazoyl)-1-methylethoxyimino]acetamido}-3-[(3-carboxy-5-trifluoromethylpyrazolo[1,5-a]pyrimidin-7-yl)-thiomethyl]-3-cephem-4-carboxylic acid MS: 881 (M+H$^+$)
IR: KBr 1772 cm$^{-1}$
$^1$H NMR (d$_6$-DMSO) δ:
1.47 (s, 3H), 1.50 (s, 3H), 3.60 (d, 1H, J=17.5Hz), 3.70 (d, 1H, J=17.5Hz), 4.55 (s, 2H, broad), 5.23 (d, 1H, J=5Hz), 5.87 (dd, 1H, J=5Hz, J=2Hz), 7.30 (d, 1H, J=2Hz), 7.30 (d, 1H, J=2Hz), 7.30 (s, 2H, broad), 7.76 (s, 1H), 8.79 (s, 1H), 9.24 (s, 1H), 9.30 (s, 1H, broad), 9.56 (s, 1H, broad), 9.64 (d, 1H, J=8Hz), 10.00 (s, 1H), 13.0 (s, 1H, broad), 14.0 (s, 1H, broad).

EXAMPLE 63

7-{2-[2-Amino-1,3-thiazol-4-yl]-2-[1-(3-(3,4-dihydroxybenzoyl)carbazoyl)-1-methylethoxyimino]acetamido}-3-[(2-carboxy-5-trifluoromethyl-s-triazolo[1,5-a]pyrimidin-7-yl)-thiomethyl]-3-cephem-4-carboxylic acid IR: (KBr) 1774 cm$^{-1}$
$^1$H NMR (d$_6$-DMSO) δ:
1.47 (s, 3H), 1.49 (s, 3H), 3.66 (d, 1H, J=17.5Hz), 3.84 (d, 1H, J=17.5Hz), 4.60 (s, 2H, broad), 5.24 (d, 1H, J=5Hz), 5.92 (dd, 1H, J=5Hz, J=8Hz), 6.74 (d, 1H, J=7Hz), 6.87 (s, 1H), 7.24 (dd, 1H, J=8Hz, J=2Hz), 7.28 (d, 1H, J=2Hz), 7.30 (s, 2H), 7.95 (s, 1H), 9.22 (s, 2H, broad), 9.68 (d, 1H, J=8Hz), 10.01 (s, 1H), 14.10 (s, 2H, very broad).

The 7-(2-amino-1,3-thiazol-4-yl-glyoxylamide) intermediates used for making compounds in Examples 61 to 63 were prepared in the same manner as in Example 59.

EXAMPLE 64

In the same manner as in Example 13, the following compound was synthesized.
2,5-Dimethyl-7-mercaptopyrazolo[1,5-a]pyrimidine
$^1$H NHR (d$_6$-DMSO) δ:
2.36 (s, 3H), 2.42 (s, 3H), 6.28 (s, 1H), 6.75 (s, 1H.

EXAMPLE 65

In the same manner as in Example 13, the following compound was synthesized.
7-Mercapto-5-methylpyrazolo[1,5-a]pyrimidine
$^1$H NHR (d$_6$-DMSO) δ:
2.42 (s, 3H), 6.44 (d, J=2Hz, 1H), 6.83 (s, 1H), 8.21 (d, J=2Hz, 1H).

EXAMPLE 66

In the same manner as in Example 17, the following compound was synthesized.
7-Amino-3-[(2,5-dimethylpyrazolo[1,5-a]pyrimidine-7-yl)-thiomethyl]-3-cephem-4-carboxylic acid
$^1$H NHR (d$_6$-DMSO) δ:
2.68 (s, 3H), 2.92 (s, 3H), 3.90 (s, 2H), 4.95 (broad s, 2H), 5.93 (s, 2H), 6.79 (s, 1H), 7.38 (s, 1H).

EXAMPLE 67

In the same manner as in Example 17, the following compound was synthesized.
7-Amino-3-[(5-methylpyrazolo[1,5-a]pyrimidin-7-yl)thiomethyl]-3-cephem-4-carboxylic acid
$^1$H NHR (d$_6$-DMSO) δ:
2.90 (s, 3H), 3.88 (s, 2H), 4.80–5.03 (m, 2H), 5.49 (s, 2H), 7.00 (d, J=2Hz, 1H), 7.48 (s, 1H), 8.64 (d, J=2Hz, 1H).

EXAMPLE 68

In the same manner as in Example 34, the following compound was synthesized.
7-Mercapto-5-methyl-2-trifluoromethyl-s-triazolo[1,5-a]pyrimidine
$^1$H NHR (d$_6$-DMSO) δ:
2.38 (s, 3H), 7.10 (s, 1H).

EXAMPLE 69

In the same manner as in Example 35, the following compound was synthesized.
7-Amino-3-[(5-methyl-2-trifluoromethyl-s-triazolo[1,5-]pyrimidine-7-yl)thiomethyl]-3-cephem-4-carboxylic acid
$^1$H NHR (d$_6$-DMSO) δ:
3.01 (s, 3H), 3.92 (s, 2H), 5.00 (ABq, J=7Hz, 12Hz, 2H), 5.60 (m, 2H), 7.92 (s, 1H).

TEST EXAMPLE 5

The minimum inhibition concentrations (MIC) of the compounds obtained in the respective examples described above were measured according to the standard method of Japanese Chemotherapy Association. The results are shown in Table 7 and Table 8.

As is apparent from Table 7, the compounds of the present invention is effective to gram positive bacteria and gram negative bacteria and have wide range of antibacterial spectrum. Particularly, the compounds of the present invention exhibit strong antibacterial activities to glucose non-fermentable bacteria including Pseudomonas aeruginosa when compared with those of the third aged series cephalosporin.

As is apparent from Table 8, the compounds of the present invention exhibit strong antibacterial activities against a cephazoline resistance clinical separated strain which is one of the third aged series cephalosporins.

TABLE 7

| Strain | Example | MIC (μg/ml) | | | | | | | | |
|---|---|---|---|---|---|---|---|---|---|---|
| | | 53 | 45 | 46 | 47 | 48 | 56 | 57 | 58 | 55 |
| S. aureus | Smith | 12.500 | 12.500 | 12.500 | 25.000 | 6.250 | 6.250 | 1.560 | 1.560 | 6.250 |
| | IAA498 | 12.500 | 25.000 | 25.000 | 50.000 | 12.500 | 12.500 | 3.130 | 3.130 | 6.250 |
| E. coli | ML4707 | 0.012 | 0.050 | 0.050 | 0.025 | 0.100 | 0.025 | <0.006 | <0.006 | 0.050 |
| | GN5482 | 0.012 | 0.050 | 0.050 | 0.025 | 0.050 | 0.025 | <0.006 | <0.006 | 0.025 |
| K. pneumoniae | 4at521 | 0.012 | 0.050 | 0.025 | 0.025 | 0.100 | 0.025 | 0.012 | 0.012 | 0.025 |
| E. colacae | GN7471 | 0.780 | 1.560 | 0.780 | 0.390 | 12.500 | 0.390 | 1.560 | 1.560 | 25.000 |
| | 908RN | 0.780 | 1.560 | 12.500 | 0.780 | 3.130 | 1.560 | 0.390 | 0.390 | 12.500 |
| C. freundii | GN7391 | 6.250 | 12.500 | 100.000 | 1.560 | 12.500 | 25.000 | 3.130 | 3.130 | 6.250 |
| S. marcescens | GN10857 | 0.780 | 1.560 | 0.780 | 0.390 | 12.500 | 0.390 | 1.560 | 1.560 | 1.560 |
| P. vulgaris | GN7919 | 1.560 | 3.130 | 12.500 | 6.258 | 3.130 | 1.560 | 0.780 | 1.560 | 1.560 |
| P. aeruginosa | GN10362 | 0.050 | 0.200 | 0.200 | 0.390 | 0.780 | 0.100 | 0.100 | 0.100 | 0.390 |
| | 4au542 | 0.050 | 0.200 | 0.390 | 0.780 | 1.560 | 0.200 | 0.100 | 0.200 | 0.390 |
| | 5D58-1 | 0.100 | 0.100 | 0.200 | 0.390 | 0.780 | 0.050 | 0.100 | 0.050 | 0.390 |
| P. cepacia | OF189 | <0.006 | 0.012 | <0.006 | <0.006 | <0.006 | <0.006 | 0.012 | 0.012 | 0.050 |
| P. maltophilia | OF247 | 0.780 | 1.560 | 0.780 | 0.780 | 12.500 | 0.390 | 1.560 | 1.560 | 1.560 |

TABLE 8

| Strain | Example | MIC (μg/ml) | | | | | | | | |
|---|---|---|---|---|---|---|---|---|---|---|
| | | 53 | 45 | 46 | 47 | 48 | 56 | 57 | 58 | CAZ |
| E. cloacae | 5D52-2 | 0.100 | 0.390 | 0.390 | 0.200 | 1.560 | 0.100 | 0.100 | 0.100 | 12.500 |
| | 5D63-2 | 0.390 | 0.780 | 5.250 | 0.390 | 1.560 | 1.560 | 0.390 | 0.390 | 12.500 |
| | 1V25 | 6.250 | 6.250 | 25.000 | 3.130 | 50.000 | 12.500 | 6.250 | 6.250 | 25.000 |
| | 1V247 | 12.500 | 6.250 | 25.000 | 3.130 | 50.000 | 12.500 | 6.250 | 6.250 | 12.500 |
| C. freundii | 5D60-1 | 3.130 | 3.130 | 12.500 | 0.780 | 12.500 | 6.250 | 1.560 | 1.560 | >100 |
| | 1R523 | 0.780 | 0.780 | 3.130 | 0.390 | 0.780 | 1.560 | 0.200 | 0.390 | 25.000 |
| | 1R524 | 0.780 | 0.780 | 3.130 | 0.390 | 0.780 | 1.560 | 0.200 | 0.390 | 25.000 |
| | 1R526 | 0.780 | 1.560 | 3.130 | 0.390 | 12.500 | 3.130 | 1.565 | 3.130 | 25.000 |
| | 1R527 | 0.780 | 3.130 | 3.130 | 0.780 | 25.000 | 1.560 | 3.130 | 1.560 | 25.000 |
| | 1U589 | 3.130 | 3.130 | 6.250 | 1.560 | 12.500 | 6.250 | 3.130 | 3.130 | 100 |

TABLE 8-continued

| Strain | Example | \multicolumn{9}{c}{MIC (μg/ml)} |
| | | 53 | 45 | 46 | 47 | 48 | 56 | 57 | 58 | CAZ |
| --- | --- | --- | --- | --- | --- | --- | --- | --- | --- | --- |
| | 1U692 | 1.560 | 1.560 | 6.250 | 0.390 | 12.500 | 6.250 | 1.560 | 1.560 | 50.000 |

EXAMPLE 64

The following pharmaceuticals for injection were prepared.

Pharmaceutical for injection 1:
7-{2-[2-Amino-1,3-thiazol-4-yl]-2-[1-(3-(3,4-dihydroxy-benzoyl)carbazoyl)-1-methylethoxyimino]acetamide}-3-carbamoyloxymethyl-3-cephem-4-carboxylic acid.sodium salt
obtained in Example 1  500 mg
Sterile distilled water  amount so as to give the total amount of 5 ml Pharmaceutical for injection 2:
7-{2-[2-Amino-1,3-thiazol-4-yl]-2-[1-(3-(3,4-dihydroxy-benzoyl)carbazoyl)-1-methylethoxyimide]acetamide}-3-[(2-carboxy-5-methyl-s-triazolo[1,5-a]pyrimidin-7-yl)thiomethyl]-3-cephem-4-carboxylic acid sodium salt obtained in
Example 2  500 mg
Sterile distilled water  amount so as to give the total amount of 5 ml The above compounds were dissolved in the sterile distilled water, respectively, to obtain the pharmaceuticals for injection 1 and 2.

We claim:

1. A β-lactam compound represented by the formula (I):

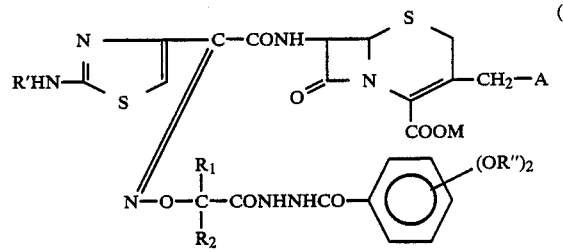

wherein $R_1$ and $R_2$ are independently a hydrogen atom or a lower alkyl group; M is a hydrogen atom, a protective group selected from the group consisting of a diphenyl methyl group, a t-butyl group, a p-nitrobenzyl group, and a trimethyl silyl group or an eliminatable group which is easily hydrolyzable in a human body selected from the group consisting of an acetoxymethyl group, an α-acetoxyethyl group, a pivaroyl-oxymethyl group, an α-ethoxycarbonyloxymethyl group, an α-methoxycarbonyloxymethyl group, an α-methoxycarbonyloxyethyl group, an α-ethoxycarbonyloxyethyl group, a 1-indanyl group, a phthalidyl group and a 5-methyl-2-oxo-1,3-dioxol-4-yl-methyl group; R' and R'' are independently a hydrogen atom or a protective group selected from the group consisting of acetyl group, a propionyl group, a methoxycarbonyl group and an ethoxycarbonyl group; A is group represented by the following formula (b), (c), or (d) or (e):

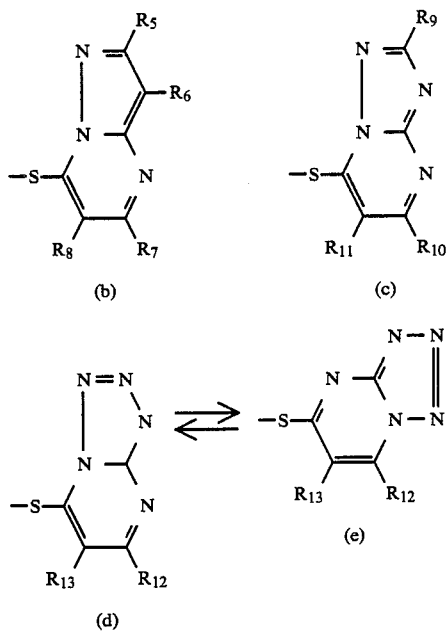

wherein $R_5$, $R_6$, $R_7$, $R_8$, $R_9$, $R_{10}$, $R_{11}$, $R_{12}$ and $R_{13}$ represent independently a hydrogen atom, a cyano group, a lower alkyl group which may be substituted by a halogen atom, a cycloalkyl group containing 3 to 6 carbon atoms or a carboxyl group which may be substituted by a protective group selected from the group consisting of a diphenyl methyl group, a t-butyl group, a p-nitrobenzyl group, and a trimethyl silyl group, or an eliminatable group which is easily hydrolyzable in a human body selected from the group consisting of an acetoxymethyl group, an α-acetoxyethyl group, a pivaroyl-oxymethyl group, an α-ethoxycarbonyloxymethyl group, an α-methoxycarbonyloxymethyl group, an α-methoxycarbonyloxyethyl group, an α-ethoxycarbonyloxyethyl group, a 1-indanyl group, a phthalidyl group and a 5-methyl-2-oxo-1,3-dioxol-4-yl-methyl group and further, $R_7$ and $R_8$, $R_{10}$ and $R_{11}$, and $R_{12}$ and $R_{13}$ may be combined with each other, respectively, to form an alkylene group having 3 to 4 carbon atoms and its pharmaceutically acceptable salt.

2. A β-lactam compound or its pharmaceutically acceptable salt according to claim 1, wherein said compound is 7-{2-[2-amino-1,3-thiazol-4-yl]-2-[1-(3-(3,4-dihydroxybenzoyl)carbazoyl)-1-methylethoxyimino]acetamide}-3-[(3-carboxy-5-methyl-pyrazolo[1,5-a]pyrimidin-7-yl)thiomethyl]-3-cephem-4-carboxylic acid and its pharmaceutically acceptable salt.

3. A medicinal composition for bacterially infectious disease therapy comprising a pharmaceutically acceptable carrier and, as its active ingredient, a β-lactam compound represented by the formula (I):

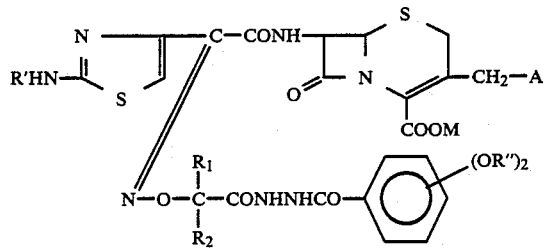

(I)

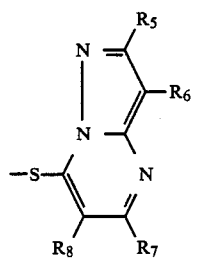 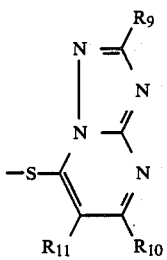

(b)      (c)

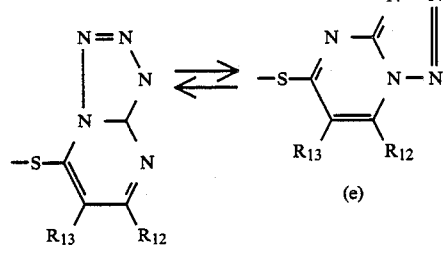

(e)

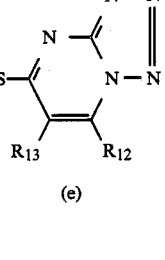

(d)

wherein $R_1$ and $R_2$ are independently a hydrogen atom or a lower alkyl group; M is a hydrogen atom, a protective group selected from the group consisting of a diphenyl methyl group, a t-butyl group, a p-nitrobenzyl group, and a trimethyl silyl group or an eliminatable group which is easily hydrolyzable in a human body selected from the group consisting of an acetoxymethyl group, an α-acetoxyethyl group, a pivaroyl-oxymethyl group, an α-ethoxycarbonyloxymethyl group, an α-methoxycarbonyloxymethyl group, an α-methoxycarbonyloxyethyl group, an α-ethoxycarbonyloxyethyl group, a 1-indanyl group, a phthalidyl group and a 5-methyl-2-oxo-1,3-dioxol-4-yl-methyl group; R' and R'' are independently a hydrogen atom or a protective group selected from the group consisting of acetyl group, a propionyl group, a methoxycarbonyl group and an ethoxycarbonyl group; A is a group represented by the following formula (b), (c), or (d) or (e):

wherein $R_5$, $R_6$, $R_7$, $R_8$, $R_9$, $R_{10}$, $R_{11}$, $R_{12}$ and $R_{13}$ represent independently a hydrogen atom, a cyano group, a lower alkyl group which may be substituted by a halogen atom, a cycloalkyl group containing 3 to 6 carbon atoms or a carboxyl group which may be substituted by a protective group selected from the group consisting of a diphenyl methyl group, a t-butyl group, a p-nitrobenzyl group, and a trimethyl silyl group, or an eliminatable group which is easily hydrolyzable in a human body selected from the group consisting of an acetoxymethyl group, an α-acetoxyethyl group, a pivaroyloxymethyl group, an α-ethoxycarbonyloxymethyl group, an α-methoxycarbonyloxymethyl group, an α-methoxycarbonyloxyethyl group, an α-ethoxycarbonyloxyethyl group, a 1-indanyl group, a phthalidyl group and a 5-methyl-2-oxo-1,3-dioxol-4-yl-methyl group and further, $R_7$ and $R_8$, $R_{10}$ and $R_{11}$, and $R_{12}$ and $R_{13}$ may be combined with each other, respectively, to form an alkylene group having 3 to 4 carbon atoms and its pharmaceutically acceptable salt.

4. A compound represented by the formula (IV):

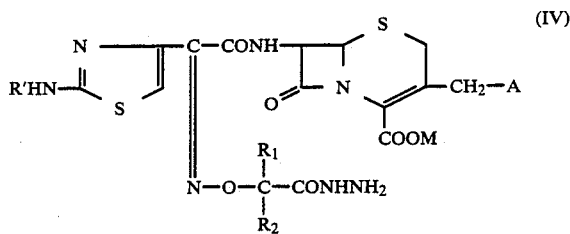

(IV)

wherein $R_1$ and $R_2$ are independently a hydrogen atom or a lower alkyl group; M is a hydrogen atom, a protective group selected from the group consisting of a diphenyl methyl group, a t-butyl group, a p-nitrobenzyl group, and a trimethyl silyl group or an eliminatable group which is easily hydrolyzable in a human body selected from the group consisting of an acetoxymethyl group, an α-acetoxyethyl group, a pivaroyl-oxymethyl group, an α-ethoxycarbonyloxymethyl group, an α-methoxycarbonyloxymethyl group, an α-methoxycarbonyloxyethyl group, an α-ethoxycarbonyloxyethyl group, a 1-indanyl group, a phthalidyl group and a 5-methyl-2-oxo-1,3-dioxol-4-yl-methyl group; R' and R'' are independently a hydrogen atom or a protective group selected from the group consisting of acetyl group, a propionyl group, a methoxycarbonyl group and an ethoxycarbonyl group; A is a group represented by the following formula (b), (c) or (d) or (e):

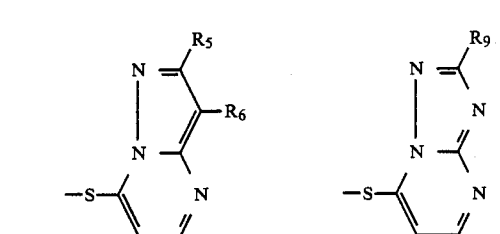

(b)      (c)

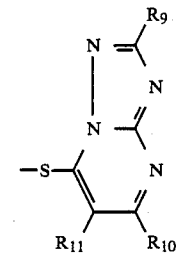

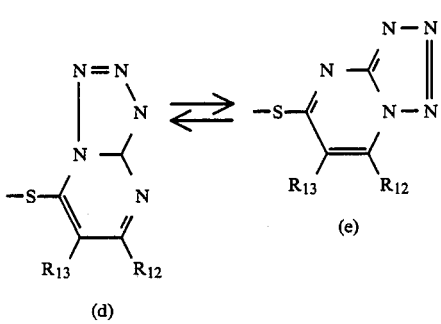

(e)

(d)

wherein $R_5$, $R_6$, $R_7$, $R_8$, $R_9$, $R_{10}$, $R_{11}$, $R_{12}$ and $R_{13}$ represent independently a hydrogen atom, a cyano group, a lower alkyl group which may be substituted by a halogen atom, a cycloalkyl group, containing 3 to 6 carbon atoms or a carboxyl group which may be substituted by a protective group selected from the group consisting of a diphenyl methyl group, a t-butyl group, a p-nitrobenzyl group, and a trimethyl silyl group, or an eliminatable group which is easily hydrolyzable in a human body selected from the group consisting of an acetoxymethyl group, an α-acetoxyethyl group, a pivaroyloxymethyl group, an α-ethoxycarbonyloxymethyl group, an α-methoxycarbonyloxymethyl group, an α-methoxycarbonyloxyethyl group, an α-ethoxycarbonyloxyethyl group, a 1-indanyl group, a phthalidyl group and a 5-methyl-2-oxo-1,3-dioxol-4-yl-methyl group and further, $R_7$ and $R_8$, $R_{10}$ and $R_{11}$, and $R_{12}$ and $R_{13}$ may be combined with each other, respectively, to form an alkylene group having 3 to 4 carbon atoms and its pharmaceutically acceptable salt.

5. A β-lactam compound according to claim 1, wherein said compound is 7-{2-[2-amino-1,3thiazol-4-yl]-2-[(3-(3,4-dihydroxybenzoyl)carbazoyl)methoxyimino]acetamide}-3-[(2-carboxy-5-methyl-s-triazolo[1,5-a]pyrimidin-7-yl)thiomethyl]-3-cephem-4-carboxylic acid and its pharmaceutically acceptable salt.

6. A β-lactam compound according to claim 1, wherein said compound is 7-{2-[2-amino-1,3-thiazol-4-yl]-2-[1-(3-(3,4-dihydroxybenzoyl)carbazoyl)ethoxyimino)acetamide}-3-[(2-carboxy-5-methyl-s-triazolo[1,5-a]pyrimidin-7-yl)thiomethyl]-3-cephem-4-carboxylic acid and its pharmaceutically acceptable salt.

7. A β-lactam compound according to claim 1, wherein said compound is 7-{2-[2-amino-1,3-thiazol-4-yl]-2-[(3-(3,4-dihydroxybenzoyl)carbazoyl)methoxyimino]acetamide}-3-[(5methyl-s-triazolo[1,5-a]pyrimidin-7-yl)thiomethyl]-3-cephem-4-carboxylic acid and its pharmaceutically acceptable salt.

8. A β-lactam compound according to claim 1, wherein said compound is 7-{2-[2-amino-1,3-thiazol-4-yl]-2-[1-(3-(3,4-dihydroxybenzoyl)carbazoyl)ethoxyimino]acetamide}-3-[(5-methyl-s-triazolo[1,5-a]pyrimidin-7-yl)thiomethyl]-3-cephem-4-carboxylic acid and its pharmaceutically acceptable salt.

9. A β-lactam compound according to claim 1, wherein said compound is 7-{2-[2-amino-1,3-thiazol-4-yl]-2-[1-(3-(3,4-dihydroxybenzoyl)carbazoyl)-1-methylethoxyimino]acetamide}-3-[(5-methyl-s-triazolo[1,5-a]pyrimidin-7-yl)thiomethyl]-3-cephem-4-carboxylic acid and its pharmaceutically acceptable salt.

10. A β-lactam compound according to claim 1, wherein said compound is 7-{2-[2-amino-1,3-thiazol-4-yl]-2-[1-(3-(3,4-dihydroxybenzoyl)carbazoyl)-1-methylethoxyimino]acetamide}-3-[(2-carboxy-6,7-dihydro-5H-cyclopenta[f]-s-triazolo[1,5-a]pyrimidin-8-yl)thiomethyl]-3-cephem-4-carboxylic acid and its pharmaceutically acceptable salt.

11. A β-lactam compound according to claim 1, wherein said compound is 7-{2-[2-amino-1,3-thiazol-4-yl]-2-[1-(3-(3,4-dihydroxybenzoyl)carbazoyl)-1-methylethoxyimino]acetamide}-3-[(6,7-dihydro-5H-cyclopenta[f]-s-triazolo[1,5-a]pyrimidin-8-yl)-thiomethyl]-3-cephem-4-carboxylic acid and its pharmaceutically acceptable salt.

12. A β-lactam compound according to claim 1, wherein said compound is 7-{2-[2-amino-1,3-thiazol-4-yl]-2-[1-(3-(3,4-dihydroxybenzoyl)carbazoyl-1-methylethoxyimino]acetamide}-3-[(5-carboxy-2-methyl-s-triazolo[1,5-a]pyrimidin-7-yl)-thiomethyl]-3-cephem-4-carboxylic acid and its pharmaceutically acceptable salt.

13. A β-lactam compound according to claim 1, wherein said compound is 7-{2-[2-amino-1,3-thiazol-4-yl]-2-[1-(3-(3,4-dihydroxybenzoyl)carbazoyl)-1-methylethoxyimino]acetamide}-3-[(s-triazolo[1,5-a]pyrimidin-7-yl)thiomethyl]-3-cephem-4-carboxylic acid and its pharmaceutically acceptable salt.

14. A β-lactam compound according to claim 1, wherein said compound is 7-{2-[2-amino-1,3-thiazol-4-yl]-2-[1-(3-(3,4-dihydroxybenzoyl)carbazoyl)-1-methylethoxyimino]acetamide}-3-[(5,6-dimethyl-s-triazolo[1,5-a]pyrimidin-7-yl)thiomethyl]-3-cephem-4-carboxylic acid and its pharmaceutically acceptable salt.

15. A β-lactam compound according to claim 1, wherein said compound is 7-{2-[2-amino-1,3-thiazol-4-yl]-2-[1-(3-(3,4-dihydroxybenzoyl)carbazoyl)-1-methylethoxyimino]acetamide-3-[(2-carboxy-s-triazolo[1,5-a]pyrimidin-7-yl)thiomethyl]-3-cephem-4-carboxylic acid and its pharmaceutically acceptable salt.

16. A β-lactam compound according to claim 1, wherein said compound is 7-{2-[2-amino-1,3-thiazol-4-yl]-2-[1-(3-(3,4-dihydroxybenzoyl)carbazoyl)-1-methylethoxyimino]acetamide}-3-[(2-carboxy-5,6-dimethyl-s-triazolo[1,5-a]pyrimidin-7-yl)thiomethyl]-3-cephem-4-carboxylic acid and its pharmaceutically acceptable salt.

17. A β-lactam compound according to claim 1, wherein said compound is 7{2-[2-amino-1,3-thiazol-4-yl]-2-[1-(3-(3,4-diacetoxybenzoyl)carbazoyl)-1-methylethoxyimino]acetamido}-3-[(2-carboxy-5-methyl-s-triazolo[1,5-a]pyrimidin-7-yl)thiomethyl]-3-cephem-4-carboxylic acid and its pharmaceutically acceptable salt.

18. A β-lactam compound according to claim 1, wherein said compound is 7-{2-[2-amino-1,3-thiazol-4-yl]-2-[1-(3-(3,4-diacetoxybenzoyl)carbazoyl)-1-methylethoxyimino]acetamido}-3-[(1-carboxy-s-triazolo[1,5-a]pyrimidin-7-yl)thiomethyl]-3-cephem-4-carboxylic acid and its pharmaceutically acceptable salt.

19. A β-lactam compound according to claim 1, wherein said compound is 7-{2-[2-amino-1,3-thiazol-4-yl]-2-[1-(3-(3,4-diacetoxybenzoyl)carbazoyl)-1-methylethoxyimino]acetamido}-3-[(5-methyl-2-trifluoromethyl-s-triazolo[1,5-a]pyrimidin-7-yl)thiomethyl]-3-cephem-4-carboxylic acid and its pharmaceutically acceptable salt.

20. A β-lactam compound according to claim 1, wherein said compound is 7-{2-[2-amino-1,3-thiazol-4-yl]-2-[1-(3-(3,4-diacetoxybenzoyl)carbazoyl)-1-methylethoxyimino]acetamido}-3-[(2-carboxy-6,7-dihydro-5H-cyclopenta[f]-s-triazolo[1,5-a]pyrimidine-8-yl)thiomethyl]-3-cephem-4-carboxylic acid and its pharmaceutically acceptable salt.

21. A β-lactam compound according to claim 1, wherein said compound is 7-{2-[2-amino-1,3-thiazol-4-yl]-2-[1-(3-(3,4-dihydroxybenzoyl)carbazoyl)-1-methylethoxyimino]acetamido}-3-[(5-methyl-2-trifluoromethyl-s-triazolo[1,5-a]pyrimidin-7-yl)thiomethyl]-3-cephem-4-carboxylic acid and its pharmaceutically acceptable salt.

22. A β-lactam compound according to claim 1, wherein said compound is 7-{2-[2-amino-1,3-thiazol-4-yl]-2-[1-(3-(3,4-dihydroxybenzoyl)carbazoyl)-1-methylethoxyimino]acetamido}-3-[(2-carboxy-s- triazolo[1,5-a]pyrimidin-7-yl)thiomethyl]-3-cephem-4-carboxylic acid and its pharmaceutically acceptable salt.

23. A β-lactam compound according to claim 1, wherein said compound is 7-{2-[2-amino-1,3-thiazol-4-yl]-2-[1-(3-(3,4-dihydroxybenzoyl)carbazoyl)-1-methylethoxyimino]acetamido}-3-[(5-methyl-pyrazolo[1,5-a]pyrimidin-7-yl)thiomethyl]-3-cephem-4-carboxylic acid and its pharmaceutically acceptable salt.

24. A β-lactam compound according to claim 1, wherein said compound is 7-{2-[2-amino-1,3-thiazol-4-yl]-2-[1-(3-(2,3-dihydroxybenzoyl)carbazoyl)-1-methylethoxyimino]acetamido}-3-[(2-carboxy-5-methyl-s-triazolo[1,5-a]pyrimidin-7-yl)thiomethyl]-3-cephem-4-carboxylic acid and its pharmaceutically acceptable salt.

25. A β-lactam compound according to claim 1, wherein said compound is 7-{2-[2-amino-1,3-thiazol-4-yl]-2-[1-(3-(3,4-dihyddroxybenzoyl)carbazoyl]-1-methylethoxyimin]acetamido{-3-[(2-cyano-5-methyl-s-triazolo[1,5-a]pyrimidin-7-yl)thiomethyl]-3-cephem-4-carboxylic acid and its pharmaceutically acceptable salt.

26. A β-lactam compound according to claim 1, wherein said compound is 7-{2-[2-amino-1,3-thiazol-4-yl]-2-[1-(3-(3,4-dihydroxybenzoyl)carbazoyl)-1-methylethoxyimino]acetamido}-3-[(2-carboxy-5-trifluoromethyl-s-triazolo[1,5-a]pyrimidin-7-yl)thiomethyl]-3-cephem-4-carboxylic acid and its pharmaceutically acceptable salt.

27. A β-lactam compound according to claim 1, wherein said compound is 7-{2-[2-amino-1,3-thiazol-4-yl]-2-[1-(3-(3,4-dihydroxybenzoyl)carbazoyl)-1-methylethoxyimino]acetamido}-3-[(2-carboxy-5-methyl-s-triazolo[1,5-a]pyrimidin-7-yl)thiomethyl]-3-cephem-4-carboxylic acid and its pharmaceutically acceptable salt.

* * * * *